US007875601B2

(12) United States Patent
O'Reilly et al.

(10) Patent No.: US 7,875,601 B2
(45) Date of Patent: *Jan. 25, 2011

(54) CANCER TREATMENT WITH EPOTHILONES

(75) Inventors: Terence O'Reilly, Basel (CH); Markus Wartmann, Riehen (CH); Manuel Litchman, Teaneck, NJ (US); Pamela Cohen, Tenafly, NJ (US)

(73) Assignee: Novartis AG, Basel (CH)

( * ) Notice: Subject to any disclaimer, the term of this patent is extended or adjusted under 35 U.S.C. 154(b) by 1316 days.

This patent is subject to a terminal disclaimer.

(21) Appl. No.: 11/406,896

(22) Filed: Apr. 19, 2006

(65) Prior Publication Data

US 2006/0223867 A1     Oct. 5, 2006

Related U.S. Application Data

(63) Continuation of application No. 10/633,114, filed on Aug. 1, 2003, now abandoned, which is a continuation of application No. 09/925,119, filed on Aug. 9, 2001, now Pat. No. 6,635,666, which is a continuation of application No. 09/233,993, filed on Jan. 19, 1999, now Pat. No. 6,302,838.

(30) Foreign Application Priority Data

| Feb. 25, 1998 | (GB) | ................................ 9803905.0 |
| Feb. 25, 1998 | (GB) | ................................ 9803907.6 |
| Mar. 19, 1998 | (GB) | ................................ 9805936.3 |
| Mar. 19, 1998 | (GB) | ................................ 9805937.1 |

(51) Int. Cl.
*A01N 43/00* (2006.01)
*A61K 31/33* (2006.01)

(52) U.S. Cl. .................................................. 514/183
(58) Field of Classification Search ................... 514/365
See application file for complete search history.

(56) References Cited

U.S. PATENT DOCUMENTS

| 5,716,939 | A | 2/1998 | Lundy et al. |
| 5,969,145 | A | 10/1999 | Schinzer et al. |
| 6,020,315 | A | 2/2000 | Bosslet et al. |
| 6,043,372 | A | 3/2000 | Schinzer et al. |
| 6,121,029 | A | 9/2000 | Schupp et al. |
| 6,156,905 | A | 12/2000 | Schinzer et al. |
| 6,242,469 | B1 | 6/2001 | Danishefsky et al. |
| 6,284,781 | B1 | 9/2001 | Danishefsky et al. |
| 6,288,237 | B1 | 9/2001 | Hoefle et al. |
| 6,300,355 | B1 | 10/2001 | Danishefsky et al. |
| 6,302,838 | B1 | 10/2001 | O'Reilly et al. |
| 6,348,551 | B1 | 2/2002 | Fürstner et al. |
| 6,350,878 | B1 | 2/2002 | Altmann et al. |
| 6,369,234 | B1 | 4/2002 | Danishefsky et al. |
| 6,380,394 | B1 | 4/2002 | Nicolaou et al. |
| 6,441,186 | B1 | 8/2002 | Nicolaou et al. |
| 6,605,726 | B1 | 8/2003 | Multzer et al. |
| 6,613,912 | B2 | 9/2003 | Hoefle et al. |
| 6,635,666 | B2 | 10/2003 | O'Reilly et al. |
| 6,660,758 | B1 | 12/2003 | Nicolaou et al. |
| 6,828,340 | B2 | 12/2004 | Danishefsky et al. |
| 6,831,076 | B2 | 12/2004 | Hoefle et al. |
| 2001/0034452 | A1 | 10/2001 | Hoefle et al. |
| 2003/0203876 | A1 | 10/2003 | Hoogevest |
| 2003/0203938 | A1 | 10/2003 | Nicolaou et al. |
| 2003/0220295 | A1 | 11/2003 | Vite et al. |
| 2004/0087634 | A1 | 5/2004 | Hoefle et al. |
| 2004/0127432 | A1 | 7/2004 | Nicolaou et al. |
| 2004/0142990 | A1 | 7/2004 | Hofmann et al. |
| 2004/0176429 | A1 | 9/2004 | Li et al. |
| 2004/0253697 | A1 | 12/2004 | Julien et al. |
| 2004/0260098 | A1 | 12/2004 | Danishefsky et al. |

FOREIGN PATENT DOCUMENTS

| DE | 41 38 042 | 5/1993 |
| WO | WO 93/10121 | 5/1993 |
| WO | WO 97/19086 | 5/1997 |
| WO | WO 98/25929 | 6/1998 |
| WO | WO 99/01124 | 1/1999 |
| WO | WO 99/02514 | 1/1999 |
| WO | WO 9907692 | 2/1999 |

OTHER PUBLICATIONS

Balog et al., Tetrahedron Lett., vol. 38(26), "Stereoselective Syntheses and Evaluation of Compounds in the 8-Desmethylepothilone A Series: Some Surprising Observations Regarding Their Chemical and Biological Properties," pp. 4529-4532 (1997).
Blagosklonny et al., Cancer Res., vol. 57, "Raf-1/bcl-2 Phosphorylation: A Step from Microtubule Damage to Cell Death," pp. 130-135 (1997).
Bollag et al., Cancer Res., vol. 55, "Epothilones, a New Class of Microtubule-stabilizing Agents with a Taxol-like Mechanism of Action," pp. 2325-2333 (1995).
Bollag, D.M., Exp. Opin. Invest. Drugs, vol. 6(7), "Epothilones: novel microtubule-stabilising agents," pp. 867-873 (1997).
Chou et al., Proc. Natl. Acad. Sci. USA, vol. 95, "Desoxyepothilone B: An efficacious microtubule-targeted antitumor agent with a promising in vivo profile relative to epothilone B," pp. 9642-9647 (1998).
Finlay, R., Chemistry & Industry, "Metathesis vs. metastasis: the chemistry and biology of the epothilones," pp. 991-996 (Dec. 15, 1997).
Gerth et al., J. Antibiotics, vol. 49, "Epothilons A and B: Antifungal and Cytotoxic Compounds from *Sorangium cellulosum* (Myxobacteria)—Production, Physico-chemical and Biological Properties," pp. 560-563 (1996).
Giannakakou et al., J. Biol. Chem., vol. 27, "Paclitaxel-resistant Human Ovarian Cancer Cells Have Mutant β-Tubulins That Exhibit Impaired Paclitaxel-driven Polymerization," pp. 17118-17125 (1997).

(Continued)

*Primary Examiner*—Brandon J Fetterolf
*Assistant Examiner*—Jean Cornet
(74) *Attorney, Agent, or Firm*—George R. Dohmann

(57) ABSTRACT

The invention relates to the treatment of a proliferative disease, especially according to certain treatment regimens, with an epothilone, especially with epothilone A and more preferably epothilone B; as well as to the treatment of certain cancers with such an epothilone.

36 Claims, No Drawings

OTHER PUBLICATIONS

Grever et al., Seminars in Oncol., vol. 19(6), "The National Cancer Institute: Cancer Drug Discovery and Development Program," pp. 622-638 (1992).

Höfle et al., Angew. Chem., vol. 108(13/14), pp. 1671-1672 (1996) (translated portion stapled to top of this article).

Jordan et al., Med. Res. Rev., vol. 18, "Tubulin as a Target for Anticancer Drugs: Agents Which Interact with the Mitotic Spindle," pp. 259-295 (1998).

Kowalski et al., J. Biol. Chem., vol. 272(4), "Activities of the Microtubule-stabilizing Agents Epothilones A and B with Purified Tubulin and in Cells Resistant to Paclitaxel (Taxol®)", pp. 2534-2541 (1997).

May et al., Chemical Communication, "Total synthesis of (--)-epothilone B," pp. 1597-1598 (1998).

Moasser et al., Proc. Natl. Acad. Sci. USA, vol. 95, "Farnesyl transferase inhibitors cause enhanced mitotic sensitivity to taxol and epothilones," pp. 1369-1374 (1998).

Mühlradt et al., Cancer Research, vol. 57, "Epothilone B Stabilizes Microtubuli of Macrophages Like Taxol without Showing Taxol-like Endotoxin Activity," pp. 3344-3346 (1997).

Nicolaou et al., Nature, vol. 387, "Synthesis of epothilones A and B in solid and solution phase," pp. 268-272 (1997).

Nicolaou et al., Angew. Chem. Int. Ed., vol. 36(19), "Designed Epothilones: Combinatorial Synthesis, Tubulin Assembly Properties, and Cytotoxic Action against Taxol-Resistant Tumor Cells," pp. 2097-2103 (1997).

Nicolaou et al., Angew. Chem. Int. Ed., vol. 37, "Chemical Biology of Epothilones," pp. 2014-2045 (1998).

Nicolaou et al., Chemistry & Biology, vol. 5(7), "Synthesis and biological properties of C12, 13-cyclopropyl-epothilone A and related epothilones," pp. 365-372 (1998).

Su et al., Angew. Chem. Int. Ed., vol. 36(7), "Total Synthesis of (--)-Epothilone B: An Extension of the Suzuki Coupling Method and Insights into Structure-Activity Relationships of the Epothilones," pp. 757-759 (1997).

Su et al., Angew. Chem. Int. Ed., vol. 36(19), "Structure-Activity Relationships of Epothilones and the First In Vivo Comparison with Paclitaxel," pp. 2093-2096 (1997).

Wartmann et al., Proceedings of the Amer. Assn. for Cancer Res., New Orleans, Mar. 28-31, 1998., vol. 39, "In vitro and in vivo activity profile of the microtubule-stabilizing agents epothilone A and B," p. 163, Abstract #1118 (1998).

Chou et al., Proceedings of the Amer. Assn. for Cancer Res., New Orleans, Mar. 28-31, 1998, vol. 39, "Pharmacologic comparison of epothilones and taxol," pp. 163-164, Abstract #1119 (1998).

Wolff et al., Int. J. Oncol., vol. 11, "Epothilone A induces apoptosis in neuroblastoma cells with multiple mechanisms of drug resistance," pp. 123-126 (1997).

Fojo et al., Cancer Res., vol. 45, "Reduced Drug Accumulation in Multiply Drug-resistant Human KB Carcinoma Cell Lines," pp. 3002-3007 (1985).

Akiyama et al., Somatic Cell and Molecular Genetics, vol. 11, No. 2. "Isolation and Genetic Characterization of Human KB Cell Lines Resistant to Multiple Drugs", pp. 117-126 (1985).

Meyer et al., Int. J. Cancer, vol. 43, "A Derivative of Staurosporine (CGP 41 251) Shows Selectively for Protein Kinase C Inhibition and In Vitro Anti-Proliferative as well as In Vivo Anti-Tumor Activity", pp. 851-856 (1989).

Bradley D., Drug Discovery Today, vol. 2(3), "Race to displace Taxol," pp. 87-88 (1997).

Cowden C., and Paterson, I., Nature, vol. 387, "Cancer drugs better than taxol?", pp. 238-239 (1997).

Höfle G. et al., Angew. Chem. Int. Ed. Engl., vol. 35 (13/14)_, "Epothilone A and B—Novwel 16-Membered Macrolides with Cytotoxic Activity: Isolation, Crystal Structure, and Conformation in Solution," pp. 1567-1569 (1996).

König J., Pharmazeutische Zeitung, vol. 142 (8) "Epothilon, ein neuer Wirkstoff gegen Krebs?" p. 35 (English translation attached).

Mann J., Nature, vol. 385, "Myxobacterial bounty," p. 117 (1997).

U.S. Appl. No. 11/089,269, filed Mar. 24, 2005, O'Reilly et al.

Avila, "The use of microtubule poisons on tumor cells," Cancer Journal, 10(6):315-318 (1997).

Blasius et al., "Für Wissenschaft und Praxis," Deutsche Apotheker Zeitung, 138(46):54-69 (1998).

Blum et al., "In vivo metabolism of epothilone B in tumor-bearing nude mice: identification of three new epothilone B metabolites by capillary high-pressure liquid chromatography/mass spectrometry/tandem mass spectrometry," Rapid Commun. Mass Spectrom., 15:41-49 (2001).

Bollag et al., "Epothilone, a new structural class of microtubule stabilizer," Proc. Annu. Meet. Am. Assoc. Cancer Res., vol. 36, Abstract 2711 (1995).

Brandt et al., "Epothilones A and B are potent inducers of apoptosis," Proceedings of the American Association for Cancer Research, 39:140, Abstract 957 (1998).

Buck et al., "Epothilones, a New Class of Microtubule-Stabilizing Agents with a Taxol-like Mechanism of Action," Chemtracts—Organic Chemistry, 11(9):671-677 (1998).

Chou et al., "Desoxyepothilone B is curative against human tumor xenografts that are refractory to paclitaxel," Proc. Natl. Acad. Sci. USA, 95:15798-15802 (1998).

Colburn et al., "Phase II study of single agent paclitaxel in adult patients with relapsed acute lymphocytic leukemia," Investigational New Drugs, 21:109-111 (2003).

Gensthaler, "Von Antitumorsubstanzen bis zu Pulverinhalatoren und Suramin," Pharmazeutische Zeitung, 143(49):42-45 (1998).

Hamel, "Antimitotic Natural Products and Their Interactions with Tubulin," Medicinal Research Reviews, 16(2):207-231 (1996).

Houlder, "Bones of a new cancer treatment," The Financial Times, p. 16 (May 15, 1997).

Kowalski et al., "Comparison of Novel Microtubule Polymerizing Agents, Discodermolide and Epothilone A/B, with Taxol," Molecular Biology of the Cell, vol. 6, Abstract 2137 (1995).

Lavelle, "What's new about new tubulin/microtubules binding agents?" Exp. Opin. Invest. Drugs, 4(8):771-775 (1995).

"Microbes create class of cancer fighters," Biotechnology Newswatch, p. 10 (Aug. 4, 1997).

"Neue krebshemmende Substanz entdeckt," Lebensmittel & Biotechnologie, 13(3):102 (1996).

Schackert, "Neue Hoffnung durch Epothilone," Deutsche Apotheker Zeitung, 137(47):37-38 (1997).

Schinzer et al., "Epothilone: neue Wirkstoffe gegen Krebs," Spektrum der Wissenschaft, pp. 38-43 (Aug. 1997).

Schultz et al., "Bringing biological solutions to chemical problems," Proc. Natl. Acad. Sci. USA, 90:14590-14951 (1998).

Service, "Tumor-Killer Made; How Does It Work?" Science, 274(5295):2009 (1996).

Wessjohann, "Epothilones: Promising Natural Products with Taxol-Like Activity," Angew. Chem. Int. Ed. Engl., 36(7):715-718 (1997).

Woo et al., "Phase I Targeted Systemic Exposure Study of Paclitaxel in Children with Refractory Acute Leukemias," Clinical Cancer Research, 5:543-549 (1999).

Cecil, Textbook of Medicine, $21^{st}$ Edition (2000), Goldman & Bennett (Editors), W. B. Saunders Company (Publisher), Chapter 198, pp. 1060-1074.

CANCER TREATMENT WITH EPOTHILONES

This application is a continuation of U.S. patent application Ser. No. 10/633,114, filed Aug. 1, 2003, which is a continuation U.S. patent application Ser. No. 09/925,119, filed Aug. 9, 2001, now U.S. Pat. No. 6,635,666, which is a continuation of U.S. patent application Ser. No. 09/233,993, filed Jan. 19, 1999, now U.S. Pat. No. 6,302,838, which in their entirety are herein incorporated by reference.

SUMMARY OF THE INVENTION

The invention relates to the treatment of a proliferative disease, especially according to certain treatment regimens using an epothilone, especially epothilone B; preferably of a gastrointestinal tumor, more preferably (1) a tumor of the colon and/or the rectum (colorectal tumor), especially if it is refractory to a (meaning at least one) representative of the taxane class of anti-cancer agents, in particular TAXOL® (paclitaxel in formulated form for clinical use), and/or at least one standard treatment with an other chemotherapeutic, especially 5-fluorouracil; (2) a tumor of the genitourinary tract, more preferably a tumor of the prostate, including primary and-metastatic tumors, especially if refractory to hormone treatment ("hormone refractory prostate cancer") and/or treatment with other standard chemotherapeutics; (3) an epidermoid tumor, more preferably an epidermoid head and neck tumor, most preferably a mouth tumor; (4) a lung tumor, more preferably a non-small cell lung tumor, especially any of these tumors that is refractory to treatment with one or more other chemotherapeutics (especially due to multidrug resistance), especially to-treatment with a member of the taxane class of anti-cancer agents, in particular TAXOL®; or (5) a breast tumor, more preferably one that is multidrug resistant, especially refractory to treatment with a member of the taxane class of anti-cancer agents, in particular TAXOL®; relating especially also to the treatment of a multidrug resistant lung tumor (preferably a non-small cell lung tumor), a multidrug resistant breast tumor, or a multidrug resistant epidermoid tumor, or in a broader sense of the invention to a treatment schedule for the treatment of an aforementioned or (in a broader sense of the invention) any other tumor, especially if it is refractory to one or more chemotherapeutics, especially multidrug resistant and/or TAXOL® refractory), such as a melanoma, ovarian cancer, pancreas cancer, neuroblastoma, head and neck cancer or bladder cancer, or in a broader sense renal, brain or gastric cancer; by administration of an epothilone as a cytotoxic agent, especially epothilone B; the term "treatment" also encompassing (i) a method of treatment for (=for treating of) said disease comprising administration of said cytotoxic agent (preferably an epothilone, especially epothilone B, in each case preferably together with a pharmaceutically acceptable carrier) to a warm-blooded animal, especially if in need of such treatment, in a therapeutically effective amount, in at least one treatment; (ii) the use of said cytotoxic agent, for the treatment of a proliferative disease; (iii) the use of said cytotoxic agent for the manufacture of a pharmaceutical preparation for the treatment of said proliferative disease (comprising admixing said cytotoxic agent with a pharmaceutically acceptable carrier); (iv) a pharmaceutical preparation comprising a dose of said cytotoxic agent that is appropriate for the treatment of said proliferative disease. The invention is, in a preferred embodiment, directed to the treatment of patients or patient groups where other treatments, especially standard treatment with an other chemotherapeutic, especially 5-fluorouracil; or therapy with members of the taxane class of anti-cancer agents, such as TAXOL®, have failed.

BACKGROUND OF THE INVENTION

Cancer still represents a major unmet medical need. Initial treatment of the disease is often surgery, radiation treatment or the combination, but recurrent (metastatic) disease is common. Chemotherapeutic treatments for most cancers are generally not curative, but only delay disease progression. Commonly, tumors and their metastases become refractory to chemotherapy, in an event known as development of multidrug resistance. In many cases, tumors are inherently resistant to some classes of chemotherapeutic agents [see DeVita V. T., Principles of Cancer Management: Chemotherapy. In: Cancer. Principles and Practice of Oncology. DeVita V. T. et al (eds.), 5th edition, Lippincott-Raven, Philadelphia, New York (1977), pp. 333-347; or Cleton, F. J., Chemotherapy: general aspects. In: Oxford Textbook of Oncology; Peckham, M., et al, Oxford University Press, Oxford, New York, Tokyo (1995), Vol. 1, pp. 445-453]. This is, for example, the case for lung tumors, especially non-small cell lung carcinoma, or also for epidermoid tumors, like epidermoid head and neck, especially mouth, tumors, or also for breast tumors. Other mechanisms why tumors are not treatable (are refractory to treatment) can be, for example, the presence of tubulin mutations or glutathione mediated mechanisms.

Intestinal, especially colorectal, cancer defines a special case of the unmet medical needs in cancer treatment. Initial treatment of the disease is often surgery, radiation treatment or the combination, but recurrent (metastatic) disease is common. First-line chemotherapeutic treatments for recurrent colorectal cancer include 5-fluorouracil. But this treatment provides at best delay of disease progression as the tumors usually become refractory to treatment. Chemotherapy of this refractory stage of disease involves other classical cytotoxic agents, but are all considered inadequate [see Cohen et al., Cancer of the colon. In: Cancer. Principles and Practice of Oncology; DeVita et al. (eds.), 5th edition, Lippincott Raven. Philadelphia, New York 1997, pp. 1144-1197; or Rowinsky, Ann. Rev. Med. 48, 353-74 (1997)].

Also for cancer of the genitourinary tract, especially prostate cancer, a further unmet medical need, initial treatment is as mentioned above for colorectal cancer, showing similar problems. First-line chemotherapeutic treatment for recurrent prostate cancer includes anti-androgens, and the recurrence is frequently androgen-dependent. But this treatment provides only delay of disease progression as the tumors almost always become refractory to anti-androgens within 6 months to 2 years (hormone-refractory prostate tumors). Chemotherapy of this anti-androgen refractory stage of diseases involves mitoxantrone or other classical anticancer cytotoxic agents, but all are considered as inadequate [see Oesterling et al., Cancer of the prostate. In: Cancer. Principles and Practice of Oncology. DeVita, V. T., et al. (eds.), 5th edition, Lippincott-Raven, Philadelphia, New York 1997, pp 1322-86; Sternberg, Cancers of the genitourinary tract. In: Cavalli et al. (eds.), Textbook of Medical Oncology; or Roth, B. J., Semin. Oncol. 23(6 Suppl. 14), 49-55 (1996)].

Among cytotoxic agents for the treatment of tumors, TAXOL® (paclitaxel), a microtubule stabilizing agent, has become a very important compound with a remarkable economic success [see Rowinsky E. K., The development and clinical utility of the taxane class of antimicrotubule chemotherapy agents; Ann. Rev. Med. 48, 353-374 (1997)].

However, TAXOL® has a number of disadvantages. Especially its extremely low solubility in water represents a severe problem. It has become necessary to administer TAXOL® in a formulation with Cremophor EL® (polyoxyethylated castor oil; BASF, Ludwigshafen, Germany) which has severe side effects, causing inter alia allergic reactions that in one case even were reported to have led to the death of a patient. More severely, certain tumor types are known to be refractory to treatment with TAXOL® even when the drug is administered as front-line therapy, or the tumors develop resistance to TAXOL® after multiple cycles of exposure.

Although the taxane class of antimicrotubule anti-cancer agents has been hailed as the "perhaps most important addition to the chemotherapeutic armamentarium against cancer over the past several decades" [see Rowinsky E. K., Ann. Rev. Med. 48, 353-374 (1997)] and despite the commercial success of TAXOL®, there remain limitations to TAXOL®'s efficacy. TAXOL® treatment is associated with a number of significant side effects and some major classes of solid tumors, namely colon and prostate, are poorly responsive to this compound (see Rowinsky E. K., loc. cit.). Specifically, as a single agent, TAXOL® has been considered to be poorly active clinically in colorectal, renal, prostatic, pancreatic, gastric and brain cancers [see Rowinsky E. K., loc. cit.; Bitton, R. J., et al., Drug Saf. 12, 196-208 (1995); or Arbuck, S. G., et al., J. Natl. Cancer Inst. Monogr. 15, 11-24 (1993)]. For example, the effectiveness of TAXOL® can be severely limited by acquired drug resistance mechanisms occurring via various mechanisms, such as overexpression of phosphoglycoproteins that function as drug efflux pumps.

Therefore, there exists an urgent need to find compounds and appropriate dosing regimens with these compounds expand the armamentarium of cancer treatment, especially in the majority of cases where treatment with taxanes and other anticancer compounds is not associated with long term survival.

The epothilones, especially epothilones A and B, represent a new class of microtubule stabilizing cytotoxic agents (see Gerth, K. et al., J. Antibiot. 49, 560-3 (1996); or Hoefle et al., DE 41 38 042), e.g. with the formulae:

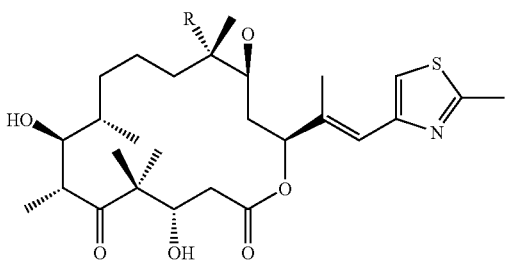

wherein R is hydrogen (epothilone A) or methyl (epothilone B).

These compounds have the following advantages:
(i) they show better water solubility than TAXOL® and are thus more appropriate for formulation; and
(ii) they have, in cell culture experiments, been reported to be active also against the proliferation of cells that, due to the activity of the P-glycoprotein efflux pump which renders them multidrug resistant, show resistance to treatment with other chemotherapeutics e.g. TAXOL® [see Bollag, D. M., et al., "Epothilones, a new class of microtubule-stabilizing agents with a Taxol-like mechanism of action", Cancer Research 55, 2325-33 (1995); and Bollag D. M., Exp. Opin. Invest. Drugs 6, 867-73 (1997)]; and
(iii) despite apparently sharing the same, or a sterically proximal binding site on the microtubule, the epothilones have been shown to be active against a TAXOL®-resistant ovarian carcinoma cell line with an altered β-tubulin [see Kowalski, R. J., et al., J. Biol. Chem. 272(4), 2534-2541 (1997)].

On the other hand, they are highly toxic and therefore their usefulness in the treatment of cancer in vivo was considered practically impossible [see, for example, PNAS 95, 9642-7 (1998)]. Therefore, the present invention shows in an unexpected way that indeed dosage regimens may be found that allow, on the one hand, to treat tumors with epothilones, especially epothilone B; and on the other hand allow for the treatment of certain patient groups that are unresponsive to other kinds of treatment, be it by multi-drug resistance, as with taxane, e.g. TAXOL®, refractoriness due to multidrug resistance, and/or any other mechanism.

The present invention has the goal to present for the first time in vivo regimens for a useful treatment with epothilones, preferably epbthilone A or especially epothilone B, that allow for the treatment of a tumor disease, e.g. a melanoma, ovarian cancer, pancreas cancer, neuroblastoma, head and neck cancer, bladder cancer, renal, brain, gastric or preferably a colorectal, prostate, breast, lung (especially non-small cell lung) or epidermoid, e.g. epidermoid head and neck, especially mouth, cancer.

While the general treatment schedule allows for the treatment of various tumor types already in front-line treatment, the invention preferably relates to the treatment of tumors that can be expected or have shown to be refractory to treatment with other chemotherapeutics, e.g. standard treatment with one or more other chemotherapeutics, especially with 5-fluorouracil and/or taxane, e.g. TAXOL® treatment.

Surprisingly, it has now been found that even the proliferation of tumor cells and tumors that are refractory to standard treatment with other chemotherapeutics, e.g. 5-fluorouracil; and/or to treatment with a member of the taxane class of compounds, most especially TAXOL®, especially of a colorectal tumor, especially one that is also refractory to standard treatment, e.g. with 5-fluorouracil; or of a lung tumor, especially a non-small cell lung cancer; an epidermoid, more preferably epidermoid head and neck, such as mouth, tumor; or a breast tumor; and/or metastasis thereof can be diminished or stopped and that even regression or tumor disappearance is possible.

DETAILED DESCRIPTION OF THE PREFERRED ASPECTS OF THE INVENTION

The present invention deals preferably with the following subject matter as part of the invention:

Whenever within this whole specification "treatment of a proliferative disease" or of a tumor, cancer or the like is mentioned, there is meant
a) a method of treatment (=for treating) of a proliferative disease, said method comprising the step of administering (for at least one treatment) an epothilone, especially epothilone A and/or B, especially B, (preferably in a pharmaceutically acceptable carrier material) to a warm-blooded animal, especially a human, in need of such treatment, in a dose that allows for the treatment of said disease (=a therapeutically effective amount), preferably in a dose (amount) as specified to be preferred hereinabove and hereinbelow;

b) the use of an epothilone, preferably epothilone A and/or B, especially epothilone B, for the treatment of a proliferative disease; or an epothilone, especially epothilone B, for use in said treatment (especially in a human);
c) the use of an epothilone, especially epothilone A and/or B, especially epothilone B, for the manufacture of a pharmaceutical preparation for the treatment of a proliferative disease; and/or
d) a pharmaceutical preparation comprising a dose of an epothilone, especially epothilone A and/or B, most especially epothilone B, that is appropriate for the treatment of a proliferative disease; or any combination of a), b), c) and d), in accordance with the subject matter allowable for patenting in a country where this application is filed;
e) a method of using an epothilone for the manufacture of a pharmaceutical preparation for the treatment of a proliferative disease, comprising admixing said epothilone with a pharmaceutically acceptable carrier. In cases where a tumor disease or a specific tumor (e.g. colon tumor, colon carcinoma or colon cancer; or prostate tumor, prostate carcinoma or prostate cancer) are mentioned instead of "proliferative disease", categories a) to e) are also encompassed, meaning that the respective tumor disease can be filled in under a) to e) above instead of "proliferative disease", in accordance with the patentable subject matter.

In a first aspect, the present invention relates to the treatment of a proliferative disease that is refractory to treatment with one or more other chemotherapeutics, where an epothilone, especially epothilone A and/or B, especially epothilone B, is administered to a warm-blooded animal, especially a human, preferably a human in need of such treatment, especially in a therapeutically effective amount.

In a second aspect, the present invention relates to an in vivo regimen for the treatment of a proliferative disease, especially a cancer that is refractory to treatment with one or more other chemotherapeutics, especially of the taxane class, like TAXOL®, and/or 5-fluorouracil, where an epothilone, especially epothilone A and/or B, especially epothilone B, is administered in a dose that is between about 1 and about 100%, preferably between about 25 and 100%, of the (single administration) maximal tolerated dose (MTD) to a warm-blooded animal, especially a human; and one or more (preferably two to seven) further doses preferably each within the dose range mentioned just above are administered in one or preferably more than one further treatment cycle(s), especially with an interval between the treatment cycles of one week or more than one week after the preceding treatment, more preferably after about one to about 6 weeks, most preferably about one to about three weeks after the preceding treatment, respectively. Generally, this treatment regimen where a high dose is administered in two or more treatment cycles with periods of time between one to six, preferably one to three weeks of time between administrations is preferred over more frequent treatments with lower doses, especially as it should reduce the frequency and duration of hospitalization and as it shows superior antitumor effects and less toxicity than more frequent treatments and more antitumor efficacy than less frequent treatment.

Preferably, for epothilone B the dose in humans to be used is calculated according to the formula (I)

$$\text{single dose (mg/m}^2\text{)}=(0.1 \text{ to } y) \times N \quad (I)$$

where N (a whole (like 1, 2 or 3) or fractional number (like 1.5 or 2.3) wherever mentioned hereinbefore and hereinafter)) is the number of weeks between treatments (preferably a number in the range of about 1 to about 6 (corresponding to an interval of about 1 to about 6 weeks), especially about 1 to about 3 (corresponding to a preferred interval of about 1 to about 3 weeks) and y is 6 or preferably 5, more preferably 4.

More preferably, the treatment dose is calculated according to the formula II $$\text{single dose (mg/m}^2\text{)}=(0.1 \text{ to } 2.5) \times N; \quad (II)$$

even more preferably according to the formula III, $$\text{single dose (mg/m}^2\text{)}=(0.1 \text{ to } 1.7) \times N; \quad (III)$$

or most preferably according to the formula IV $$\text{single dose (mg/m}^2\text{)}=(0.1 \text{ to } 1) \times N \quad (IV)$$

where, in each of formulae II to IV, N has the meaning given under formula I. For the dosages calculated according to any of the formulae I to IV, the following proviso must be met: The dose, even if calculated higher, shall not exceed about 18 mg/m$^2$ for a single administration.

Preferably, for weekly treatment the dose is between about 0.1 and about 6, preferably about 0.1 and about 5 mg/m$^2$, more preferably about 0.1 and about 3 mg/m$^2$, even more preferably 0.1 and 1.7 mg/m$^2$, most preferably about 0.3 and about 1 mg/m$^2$; for three-weekly treatment (treatment every three weeks or every third week) the dose is between about 0.3 and about 18 mg/m$^2$, preferably about 0.3 and about 15 mg/m$^2$, more preferably about 0.3 and about 12 mg/M$^2$, even more preferably about 0.3 and about 7.5 mg/m$^2$, still more preferably about 0.3 and about 5 mg/m$^2$, most preferably about 1.0 and about 3.0 mg/m$^2$. This dose is preferably administered to the human by intravenous (i.v.) administration during 2 to 180 min, preferably 2 to 120 min, more preferably during about 5 to about 30 min, most preferably during about 10 to about 30 min, e.g. during about 30 min.

Preferably, especially in the case of weekly treatment, rest periods of more than one week, more preferably of two to ten weeks, more preferably three to six weeks after the preceding treatment may be necessary after for example 3, 4, 6, 8, or more treatment cycles, depending on patient condition, to allow for sufficient recovery from the preceding treatment.

In a third aspect of the invention, the present invention relates to an in vivo regimen for the treatment of a proliferative disease, especially one that is refractory to the treatment with one or more other chemotherapeutics, where an epothilone, preferably epothilone A and/or B, especially epothilone B, is administered weekly to a warm-blooded animal, especially a human, in a dose that is below 80%, more preferably below 50% of the maximal tolerable dose (MTD).

In a fourth aspect, the invention relates to the in vivo treatment of a proliferative disease that is refractory to the treatment with one or more other chemotherapeutics, especially 5-fluorouracil or a microtubule stabilizing agent of the taxane class, especially TAXOL®, for example a multidrug resistant tumor, where an epothilone, especially epothilone B, is administered to a warm-blooded animal, especially a human.

In a fifth aspect, the invention relates to the in vivo treatment of a proliferative disease, especially one that is refractory to the treatment with one or more other chemotherapeutics, by combined administration (a) of an epothilone, preferably epothilone A and/or epothilone B, especially epothilone B, in combination with (b) another antitumor chemotherapeutic, preferably the combined treatment being timed so that component (a) and (b) are administered to a warm-blooded animal, especially a human (especially in need of such treatment), in combination in a quantity which is jointly therapeutically effective against a proliferative disease that preferably can be treated by administration of an epothilone, more preferably epothilone A and/or epothilone B, especially epothilone B; said administration preferably taking place to a human that suffers from a tumor that is refractory to other chemotherapeutic treatment, e.g. treatment especially with 5-fluorouracil or especially with a member of the taxane class of anti-cancer agents, like TAXOL®.

In this regard, the invention also relates to a combination preparation comprising components (a) and (b) as defined in the last paragraph.

The invention also relates to a product which comprises component (a) and component (b) as defined in the second paragraph above, in the presence or absence of one or more pharmaceutically acceptable carrier materials, as a combination preparation for simultaneous or chronologically staggered administration to a warm-blooded animal, especially a human, within a period of time which is small enough for the active compounds both of component (a) and of component (b) to mutually enhance antiproliferative activity especially against proliferating cells) in said warm-blooded animal, for treating a proliferative disease.

The general terms used hereinbefore and hereinafter preferably have the following meanings, if not defined otherwise:

A proliferative disease is mainly a tumor disease (or cancer) (and/or any metastases), wherever the tumor or the metastasis are located), more especially a tumor selected from the group comprising breast cancer, genitourinary cancer, lung cancer, gastrointestinal cancer, epidermoid cancer, melanoma, ovarian cancer, pancreas cancer, neuroblastoma, head and neck cancer (this term, wherever it is used, meaning a head and/or neck cancer, meaning that not only a cancer of head and neck, but also of head or neck is envisaged) or bladder cancer, or in a broader sense renal, brain or gastric cancer; more preferably (i) a tumor selected from a breast tumor; an epidermoid tumor, especially and epidermoid head and neck, preferably mouth, tumor; and a lung tumor, especially a non-small cell lung tumor; or from a gastrointestinal tumor, especially a colorectal tumor; and a genitourinary tumor, especially a prostate tumor (especially a hormone-refractory prostate tumor); or (ii) (more preferably) a proliferative disease that is refractory to the treatment with other chemotherapeutics, therapeutics, especially a corresponding tumor (and/or any metastasis), more especially a tumor selected from the group comprising tumors that are refractory to a standard treatment with (an)other chemotherapeutic(s), especially with 5-fluorouracil and/or (preferably) a microtubule stabilizing agent of the taxane class, most especially TAXOL®, still more preferably a tumor selected from gastrointestinal, e.g. colorectal (especially refractory to standard, e.g. 5-fluorouracil, and/or TAXOL® treatment); and genitourinary, e.g. prostatic tumors (and/or a metastasis thereof, especially a metastasis thereof); most preferably a gastrointestinal tumor, especially a colorectal cancer; or (iii) a tumor that is refractory to treatment with other chemotherapeutics due to multidrug resistance, especially refractory to a member of the taxane class of microtubule stabilizing agents, preferably TAXOL®, most especially a multidrug, especially TAXOL®, resistant lung tumor (especially a non-small cell lung tumor), a multidrug resistant breast tumor, or a multidrug resistant epidermoid, preferably epidermoid head and neck, most preferably mouth, tumor.

In a broader sense of the invention, a proliferative disease may furthermore be selected from hyperproliferative conditions such as hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where hereinbefore and subsequently a tumor, a tumor disease, a carcinoma or a cancer are mentioned, also metastasis in the original organ or tissue and/or in any other location are implied alternatively or in addition, whatever the location of the tumor and/or metastasis is.

The word "refractory" means that the respective proliferative disease (especially a tumor and/or any metastasis thereof), upon treatment with a (meaning at least one) chemotherapeutic other than an epothilone, shows no or only weak antiproliferative response (no or only weak inhibition of tumor growth) after the treatment with such an agent, that is, a tumor that cannot be treated at all or only with unsatisfying results with other (preferably standard) chemotherapeutics (preferably as defined above, especially 5-fluorouracil (especially in the case of colorectal, like colon, cancer), antiandrogens or preferably mitoxantrone (especially in the case of prostate cancer), or antiestrogens, like letrozole (especially in the case of breast cancer); or especially a member of the taxane class of chemotherapeutics, e.g. TAXOTERE® or TAXOL®, in a warm-blooded animal, especially a human; for example the tumor growth is not stopped, only retarded slightly or no regression is found. The present invention, where treatment of refractory tumors and the like is mentioned, is to be understood to encompass not only (a) tumor(s) where one or more chemotherapeutics have already failed during treatment of a patient, but also (a) tumor(s) that can be shown to be refractory by other means, e.g. biopsy and culture in the presence of chemotherapeutics. Where a term like "refractory against TAXOL®" is used hereinbefore and hereinafter, this term, in addition to the finished product, is also intended to mean paclitaxel, the active substance of TAXOL® "Refractory to hormone treatment" or "hormone refractory", in the case of a tumor of the genitourinary tract, especially a prostate tumor, means refractory to treatment with an antiandrogen.

TAXOL® preferably stands for the finished product that comprises paclitaxel, but, in a broader sense, is also meant to encompass paclitaxel itself of any other paclitaxel formulation with one or more carrier material(s).

Preferably, the term refractory means that with standard dose a reduction of tumor growth by less than 50% (that is a T/C % value of equal to or more than 50%) is obtained when compared with a control without chemotherapeutic, e.g. by in vivo or in vitro measurements.

Multidrug resistant tumor disease is one where resistance to one or more chemotherapeutics, including those of the taxane class, especially TAXOL®, or the anthracycline class, especially ADRIAMYCIN®, is found. The basis for this resistance is the export via an energy (especially ATP)-dependent pump located on the surface of cells of the respective tumor, especially of the P-glycoprotein family, especially P-glycoprotein (P-gp) itself. In the present invention, alternatively or in addition other mechanisms may cause a tumor to be refractory to treatment with chemotherapeutics other than an epothilone. For example, alterations in the drug target (especially microtubules in the present case), changes in the intracellular metabolism that may inactivate the compound, or changes in the physiology of the cell that would facilitate by-passing or overriding of the mechanism of drug action may lead to such resistance.

By the term "other chemotherapeutic" or "standard chemotherapeutic", there is meant especially any chemotherapeutic other than an epothilone; preferably one as defined in the introduction, especially 5-fluorouracil (especially in the case of colorectal, like colon, cancer), an anti-androgen or mitoxantrone (especially in the case of prostate cancer), or an antiestrogen, like letrozole (especially in the case of breast cancer); especially, the term refers to 5-fluorouracil or (more preferably) to members of the taxane class of microtubule stabilizing agents, such as preferably Taxotere® or more preferably TAXOL®. "Standard treatment with other chemotherapeutics", "other chemotherapeutic treatment" or "standard chemotherapy" is referring to treatment with at least one such "other" or "standard therapeutic".

By the term epothilone, any epothilone or epothilone derivative is meant. Preferably, the term "epothilone" means epothilone A, epothilone B, any epothilone derivative disclosed in WO 98/25929 (which is incorporated by reference), or any mixture thereof; more preferably, it means epothilone A and/or epothilone B, and most preferably it relates to epothilone B.

The administration in all cases mentioned above and below may take place orally but, in view of better and better defined bioavailability, more preferably is made parenterally, especially intravenously, e.g. by infusion or injection. Where subsequently "infusion" is used, this means preferably intravenous infusion, which is the most preferred mode of administration.

Subsequently, the data for adults are the basis for illustration. However, it goes without saying that the present invention also relates to the treatment of proliferative diseases in pediatrics. The doses must then be corrected in accordance with standard methods and the age, condition and other characteristics of the patient.

The Maximal Tolerated Dose (MTD) is determined according to standard procedures; preferably, in warm-blooded animals the MTD in case of oral or intravenous administration is determined as the Dose of a single administration where no death occurs and a loss of body weight of less than 40, preferably less than 25, percent (%) is found in the treated warm-blooded animal individual (this term here mainly referring to an animal; for humans see below).

The MTD may vary depending on the population of the patients which may be defined by tumor type, age range, gender, tumor stage and the like. While in animals, the most preferable way of determining the MTD can be analogous to that shown in the Examples presented below, in humans the MTD may be generally be determined by starting with one single administration of a very low dose, e.g. 1/10th of the $LD_{10}$ (i.e., the dose that is lethal to 10% of animals) in the most sensitive animal species in which toxicology studies have been performed, e.g. for epothilones (especially epothilone B) in the range from 0.1 to 25 mg/m$^2$, especially for epothilone B in the range from 0.1 to 2.5 mg/m$^2$, most especially in the range of 0.1 to 0.33 mg/m$^2$. Dose escalation for the next dose level is 100%, unless grade 2 toxicity is seen according to the US National Cancer Institute Revised Common Toxicity Criteria, in which case dose escalation will be 67%. Dose escalation for subsequent dose levels is in the range of 25% to 67%. For example, three patients are usually treated at one dose level and observed for acute toxicity for one course of treatment before any more patients are entered. If none of the three patients experience DLT (dose-limiting toxicity), then the next cohort of three patients is treated with the next higher dose. If two or more of the three patients experience DLT, then three more patients are treated at the next lower dose unless six patients have already been treated at that dose. If one of three patients treated at a dose experiences DLT, then three more patients are treated at the same level. If the incidence of DLT among those patients is one in six, then the next cohort is treated at the next higher dose. In general, if two or more of the six patients treated at a dose level experience DLT, then the MTD is considered to have been exceeded, and three more patients are treated at the next lower dose as described above. The MTD is defined as the highest dose studied for which the incidence of DLT was less than 33%. Usually dose escalation for subsequent courses in the same patient—i.e. intrapatient dose escalation—is not permitted. Alternatively, dose steps may be defined by a modified Fibonacci series in which the increments of dose for succeeding levels beyond the starting dose are 100%, 67%, 50% and 40%, followed by 33% for all subsequent levels. Finally, the MTD may be found by methods described in Simon, R., et al., J. Nat. Cancer Inst. 89(15), 1997, p. 1138-1147.

The DLT generally includes (but is not limited to) any drug-related death and most drug-related grade 3 and 4 toxicities, including febrile neutropenia (see also US National Cancer Institute Revised Common Toxicity Criteria). See especially the examples. For a human, the preferred treatment doses are defined by formula I, more preferably formula II, most preferably formula III mentioned above (with the proviso that no single dose is higher than 18 mg/m$^2$. Preferably, for weekly treatment the dose is between about 0.1 and about 6, preferably about 0.1 and about 5 mg/m$^2$, more preferably about 0.1 and about 3 mg/m$^2$, even more preferably about 0.1 and about 1.7 mg/m$^2$, most preferably about 0.3 and about 1 mg/m$^2$; for three-weekly treatment (treatment every third week) the dose is between about 0.3 and about 18 mg/m$^2$, preferably about 0.3 and about 15 mg/m$^2$, more preferably about 0.3 and about 12 mg/m$^2$, even more preferably about 0.3 and about 7.5 mg/m$^2$, still more preferably about 0.3 and about 5 mg/m$^2$, most preferably about 1.0 and about 3.0 mg/m$^2$. This dose is preferably administered to the human by intravenous (i.v.) administration during 2 to 180 min, preferably 2 to 120 min, preferably during about 5 to about 30 min, most preferably during about 10 to about 30 min, e.g. about 30 min.

From the use of animal data, the applicable doses in (adult) humans may be roughly calculated as follows:

A dose of 1 mg/kg in mouse corresponds to a dose of 3 mg/m$^2$ in a human.

By sufficient recovery from the preceding treatment, in warm-blooded animals there is meant especially the regain of body weight of the treated individual to the starting level found before the first dosing, preferably to at least 95% of said weight. In a human, the recovery from each preceding dose administration is preferably defined as recovery from any grade 3 or 4 toxicity, including e.g. achievement of a platelet count of at least 100,000/mm$^3$ and a neutrophil count of at least 1,500 cells/mm$^3$ whole blood.

Treatment can be repeated if no response is achieved after a first treatment, until tumor progression is found or until other reasons (e.g. the condition of the patient) require termination of treatment. In a human, the treatment with about 25 to about 100% of the MTD is preferably repeated every 1 to ten, especially 2 to ten weeks; preferably every 1 to 10 weeks, or every 3 to 6 weeks, until disease progression, unacceptable toxicity, 1 or preferably 2 cycles beyond determination of a complete response, or patient withdrawal of consent for any reason is encountered.

Preferably, in the case of weekly treatment of a human with epothilone, the dose is in the range of about 5 to about 60%, preferably about 10 to about 60%, e.g. about 5 to about 35% of the MTD, especially in the range of about 30 to about 35% of the MTD. Preferably, for epothilone B the dose is in the range of about 5 to about 60%, more preferably about 10 to about 60%, especially in the range of about 10 to about 45%, most especially in the range of about 30 to about 45% of the three-weekly MTD.

More preferably, treatment is stopped after the third to eighth, especially after the third to fifth weekly administration followed by a rest period of two to five, e.g. two weeks before further treatment is resumed, either by single or again weekly or twice weekly administration. Especially, in the case of weekly epothilone B treatment is stopped after the third to eighth administration followed by a rest period of two to four, e.g. two weeks before treatment is resumed by weekly administration.

Administration of component (a), that is epothilones A and/or B, especially B, takes place preferably as described above, especially using one of the special treatment regimens mentioned above.

Administration of component (b) preferably takes place according to treatment schedules that are known to the person skilled in the art.

In one preferred embodiment, component (b) is administered before component (a), preferably in a treatment comprising one or more administrations of component (b) before starting the treatment with component (a), preferably such that treatment with component (b) ends at least two, preferably 5 to 10, e.g. about 5, days prior to treatment with component (a) that is administered one or more times thereafter, preferably one to five, especially one or two times.

In a more preferred embodiment, component (a) is administered on a 3-weekly schedule before component (b), preferably in a treatment comprising one administration of component (a) before starting the treatment with component (b), more preferably such that treatment with component (a) ends immediately prior to treatment with component (b) that is administered thereafter.

In a second more preferred embodiment, component (a) is administered on a weekly schedule. Component (b), on the other hand, is administered on a 3-weekly schedule, with each administration proceeding immediately upon completion of every third administration of component (a).

In a third more preferred embodiment, component (a) is administered on a weekly schedule before component (b), preferably in a treatment comprising one administration of component (a) before starting treatment with component (b), more preferably such that treatment with component (a) ends immediately prior to treatment with component (b) that is administered thereafter.

By the term "other chemotherapeutic agent" there is meant especially any chemotherapeutic agent that is or can be used in the treatment of tumor diseases, such as chemotherapeutics derived from the following classes:
(A) Alkylating agents, preferably cross-linking chemotherapeutics, preferably bis-alkylating agents,
(B) antitumor antibiotics, preferably doxorubicin (ADRIAMYCIN®, RUBEX®);
(C) antimetabolites;
(D) plant alkaloids;
(E) hormonal agents and antagonists,
(F) biological response modifiers, preferably lymphokines or interferons
(G) inhibitors of protein tyrosine kinases and/or serine/threonine kinases,;
(H) antisense oligonucleotides or oligonucleotide derivatives; or
(I) miscellaneous agents or agents with other or unknown mechanism of action.

By the term "jointly therapeutically effective against a proliferative disease that can be treated ted by administration of epothilone A and/or epothilone B, especially epothilone B", there is preferably meant a proliferative disease as mentioned above, especially a tumor disease, the response preferably manifesting itself in a diminished proliferation, e.g. diminished tumor growth or even (more preferably) tumor regression or (most preferably) tumor disappearance ("complete response").

Preferably, the term "quantity which is jointly therapeutically effective against a proliferative disease that can be treated by administration of epothilone A and/or epothilone B, especially epothilone B" means any quantity of the components (a) and (b) of the combinations that, in the combination, is diminishing proliferation of cells responsible for any of the mentioned proliferative diseases, especially tumor (including metastatic) cells (especially diminished tumor growth) or, preferably, even causing regression, more preferably even the partial or complete disappearance, of such cells (especially tumor regression, preferably complete response meaning disappearance of the tumor(s)). This term not only comprises combinations of any component (a) and (b) where (a) and (b) are dosed in such a manner as to be antiproliferatively effective already without combination, but also doses of any such component which alone would show no or only marginal effect but which in combination leads to clearly antiproliferative effects, that is to diminished proliferation or preferably even to regression of the proliferating cells or even to cure from the proliferative disease. In addition, here the term "combination" is not only used to describe fixed combinations of the components, but also any combination of components (a) and (b) for simultaneous or chronologically staggered use within a period of time which is small enough for the active compounds both of component (a) and of component (b) to mutually enhance antiproliferative activity, e.g. in a patient.

By the term "combination preparation comprising component (a) and (b)" there is meant any combination, be it as kit of parts or as a single combined combination, of component (a) and (b) in the form of a pharmaceutical product, that is preferably where a pharmaceutically acceptable carrier material is present. For the preferred carrier materials, see below under "Pharmaceutical Preparations".

By the term "a product which comprises component (a) and component (b)", there is preferably meant a product that comprises
(a) at least one compound selected from epothilone A and (preferably) epothilone B and
(b) at least one other chemotherapeutic agent in the presence or absence of one or more pharmaceutically acceptable carrier materials, as a combination preparation, for simultaneous or chronologically staggered use, preferably within a period of time which is small enough for the active compounds both of component (a) and of component (b) to mutually enhance antiproliferative activity against proliferating cells, especially in a patient, for treating a proliferative disease which responds to such active compounds", especially a "kit of parts" in the sense that the effective components (a) and (b) of the combination can be dosed independently or by use of different fixed combinations with distinguished amounts of any components (a) and (b) at different time points. The "parts" of the kit of parts can then be administered simultaneously or chronologically staggered, that is at different time points and with equal or different time intervals for any part of the kit of parts, preferably with the condition that the time intervals are chosen such that the effect on the proliferative disease in the combined use of the parts is larger than the effect which would be obtained by use of only any one of component (a) and (b) alone or by use of both in a way that the compounds act independently (e.g. with long enough periods to avoid effects of each of the components on the others), that is, stronger inhibition of proliferation or, preferably, stronger regression or even cure of the proliferative disease is found than when the same dose of only one of components (a) and (b) is administered alone in the same dose or after sufficiently long time intervals that mutual effects of the components (a) and (b) are excluded. That is meant by the term "to mutually enhance antiproliferative activity against proliferating cells, especially in a patient"; preferably, there is meant a mutual enhancement of the effect of the components (a) and (b), especially a synergism and/or the causing of regression of the proliferating cells, up to and including their complete destruction, and especially a strong synergism between components (a) and (b).

By the term "proliferating cells", especially pathologically or abnormally proliferating cells are meant, such as tumor and/or tumor mettasasis cells, especially of tumors as defined herein as being preferred.

Preferred are combinations which show enhanced antiproliferative activity when compared with the single components alone, especially combinations that show synergism (synergistic combinations) or combinations that lead to regression of proliferative tissues and/or cure from proliferative diseases.

The term "synergism" is standing for an effect that is stronger than additive, that is, a stronger effect of the combination of any component (a) with any component (b) than could be reached by the factor of diminution of proliferation obtained from mere multiplication of the factor of diminution of proliferation for any component (a) alone or any component (b) alone when compared to a control without treatment when each (a) and (b) as such, whether alone or in combination, is administered in the same dose as in the single treatment without combination (which does not mean that the dose of (a) must be identical to that of (b), although this may also be the case). As theoretical example for mere illustration, if a component (a) alone gives a growth of tumor cells that is diminished by a factor of 2 in comparison to a control without any treatment and a component (b) alone gives a diminution of growth by a factor of 1.5, then an additive effect would be one where, by combined use of component (a) and component (b), a 3-fold diminution of growth would be found (multiplication of 2 with 1.5). A synergistic effect would for example be present if a more than 3-fold diminution of proliferation is found. The presence of synergism can be shown by this fractional product method [Webb, in: "Enzymes and Metabolic Inhibitors", Vol. 1, 66-73 and 488-512, Academic Press, New York] or alternatively by the isobologram method [see references in: Berenbaum Pharmacol. Rev. 41, 99-141 (1984)], and/or the combination index (CI) calculation method [Chou et al., Trends Pharmacol. Sci. 4, 450-454 (1983); or Chou et al., New Avenues in Developmental Cancer Chemotherapy; Bristol-Myers Symposium Series, K. R. Harrap and I. A. Connors (eds.), 37-64, New York, Academic Press (1987)].

The term "pharmaceutically acceptable carrier materials" is explained below in the definition of pharmaceutical preparations.

Provided that in the respective molecule salt-forming groups are present, component (b) (other chemotherapeutic (s)) may also be present in the form of salts wherever it is mentioned above or below.

Termination of treatment preferably takes place when either of the following occurs: Disease progression, for example under the Southwest Oncology Group (SWOG) response criteria; unacceptable toxicity (e.g. to the patient, the investigator, or both); treatment 2 cycles beyond determination of a complete response, for example under the Southwest Oncology Group (SWOG) response criteria; or patient withdrawal of consent.

Salts of components are especially acid addition salts, salts with bases or, when several salt-forming groups are present, optionally also mixed salts or internal salts. Salts are especially the pharmaceutically acceptable, e.g. substantially non-toxic, salts.

Such salts are formed, for example, from chemotherapeutics having an acidic group, for example a carboxy, phosphodiester or phosphorothioate group, and are, for example, their salts with suitable bases, such as non-toxic metal salts derived from metals of groups Ia, Ib, IIa and IIb of the Periodic Table of Elements, especially suitable alkali metal salts, for example lithium, sodium or potassium salts, or ammonium salts, also those salts that are formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl) amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)-amines, such as N,N-dimethyl-N-(2-hydroxyethyl)-amine or tri-(2-hydroxyethyl)-amine, or N-methyl-D-glucamine, or quaternary ammonium salts, such as tetrabutylammonium salts. The chemotherapeutics having a basic group, for example an amino or imino group, can form acid addition salts, for example with inorganic acids, for example a hydrohalic acid, such as hydrochloric acid, sulfuric acid or phosphoric acid, or with organic carboxylic, sulfonic, sulfo or phospho acids or N-substituted sulfamic acids, such as, for example, acetic acid, propionic acid, glycolic acid, succinic acid, maleic acid, hydroxymaleic acid, methylmaleic acid, fumaric acid, malic acid, tartaric acid, gluconic acid, citric acid, or benzoic acid, also with amino acids, for example, $\alpha$-amino acids, and also with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, N-cyclohexylsulfamic acid (with formation of the cyclamates) or with other acidic organic compounds, such as ascorbic acid. Compounds having acidic and basic groups can also form internal salts. If more than one salt-forming group is present, it is also possible that mixed salts are present.

Where hereinbefore and hereinafter numerical terms are used, they are meant to include the numbers representing the upper and lower limits. For example, "between 1 and 3" stands for a range "from and including 1 up to and including 3", and "in the range from 1 to 3" would stand for "from and including 1 up to and including 3". The same is true where instead of numbers (e.g. 3) words denoting numbers are used (e.g. "three").

Where "comprising" is used, this can preferably be replaced by "consisting essentially of", more preferably by "consisting of".

Where "about" is used in connection with a number, this preferably means the number ±15%, more preferably the number plus 5%, most preferably the number itself without "about". For example, "about 100" would stand for "from and including 85 to and including 115". Where "about" is used in connection with numeric ranges, for example "about 1 to about 3", or "between about one and about three", preferably the definition of "about" given for a number in the last sentence is applied to each number defining the start and the end of a range separately. Preferably, where "about" is used in connection with any numerical values, the "about" can be deleted.

"Weekly" stands for "about once a week" (meaning that more than one treatment is made with an interval of about one week between treatments), the about here preferably meaning ±1 day (that is, translating into "every 6 to 8 days"); most preferably, "weekly" stands for "once every 7 days".

"3-weekly" or "three-weekly" stands for "about once every three weeks" (meaning that more than one treatment is made with an interval of about three weeks between treatments), the about here preferably meaning ±3 days (that is, translating into every 18 to 24 days); most preferably, "weekly" stands for "once every 21 days" (=every third week).

PREFERRED EMBODIMENTS OF THE INVENTION

In the following preferred embodiments of the invention, the general definitions may be replaced by the more specific definitions given hereinbefore and hereinafter, as appropriate.

(1) The present invention relates especially to the treatment of a proliferative disease, especially a cancer, especially a cancer that is refractory to treatment with other chemotherapeutics and/or a member of the taxane class of anti-cancer agents, especially TAXOL®, more especially one of the preferred diseases as defined above or below, characterized in that an epothilone, especially epothilone A or most especially epothilone B, is administered more than once with a weekly up to three-weekly interval to a human in a dose that is calculated according to the formula (I)

$$\text{single dose (mg/m}^2\text{)}=(0.1 \text{ to } y) \times N \quad (I)$$

where N (a whole or fractional number) is the number of weeks between treatments (about one to about three weeks), that is N is about 1 to about 3; more preferably, the treatment dose is calculated according to the formula II $$\text{single dose (mg/m}^2\text{)}=(0.1 \text{ to } 2.5) \times N; \quad (II)$$

even more preferably according to the formula III, $$\text{single dose (mg/m}^2\text{)}=(0.1 \text{ to } 1.7) \times N; \quad (III)$$

or still more preferably according to the formula IV $$\text{single dose (mg/m}^2\text{)}=(0.1 \text{ to } 1) \times N \quad (IV)$$

where, in each of formulae II to IV, N is about 1 to about 3 (corresponding to intervals of about 1 to about 3 weeks between treatments);

the epothilone, especially epothilone B, administration preferably taking place
  (a) weekly in a human in a dose that lies between about 0.1 and about 6, preferably about 0.1 and about 5 mg/m$^2$, more preferably about 0.1 and about 3 mg/m$^2$, even more preferably about 0.1 and about 1.7 mg/m$^2$, most preferably about 0.3 and about 1 mg/m$^2$; or
  (b) three-weekly in a human in a dose that lies dose is between about 0.3 and about 18 mg/m$^2$, preferably about 0.3 and about 15 mg/m$^2$ more preferably about 0.3 and about 12 mg/m$^2$, even more preferably about 0.3 and about 7.5 mg/m$^2$, still more preferably about 0.3 and about 5 mg/m$^2$, most preferably about 1.0 and about 3.0 mg/m$^2$;
the administration preferably taking place by i.v. infusion during 2 to 120 min, more preferably during about 5 to about 30 min, most preferably during about 10 to about 30 min, e.g. during about 30 min.

(2) The present invention preferably relates also to the treatment of a tumor disease that is refractory to the treatment with an other chemotherapeutic, especially selected from 5-fluorouracil and preferably a microtubule stabilizing agent of the taxane class, most especially TAXOL®, said tumor being selected from a gastrointestinal, e.g. colorectal; a renal; a genitourinary, e.g. prostatic; a pancreatic; and a brain tumor (and/or any metastasis thereof), most preferably a gastrointestinal tumor, especially a colorectal cancer, more especially a gastrointestinal cancer, especially a colorectal cancer, that is refractory to treatment with a member of the taxane class of anti-cancer agents, especially TAXOL®, or very especially such tumor that is refractory to a standard chemotherapy, such as treatment a standard chemotherapeutic, especially with 5-fluorouracil; or a tumor of the genitourinary tract, especially a prostate cancer, most especially a hormone-refractory prostate cancer; where epothilone A and/or B, especially epothilone B, is administered to a warm-blooded animal, especially a human.

(3) The present invention preferably also relates to the treatment of a tumor disease, especially a lung tumor, especially a non-small cell lung carcinoma, especially such lung cancer that is refractory to treatment with a member of the taxane class of anti-cancer agents, especially TAXOL®; a breast tumor, especially one that is multidrug resistant; or an epidermoid tumor, preferably an epidermoid head and neck, especially mouth, tumor, especially if the latter is multidrug resistant and/or resistant to treatment with a member of the taxane class of anti-cancer agents, in particular TAXOL®; where epothilone A and/or B, especially epothilone B, is administered to a warm-blooded animal, especially a human.

(4) The present invention also preferably relates to an in vivo regimen for the treatment of a tumor disease, especially (i) of a tumor of the gastrointestinal tract, most especially a tumor of the colon and/or rectum (colorectal tumor); and/or (ii) a tumor of the genitourinary tract, especially a prostate tumor (preferably a hormone-refractory prostate tumor); especially where such tumor is refractory to treatment with an other chemotherapeutic, especially one of the taxane class, most especially TAXOL®; where epothilone A and/or B, especially epothilone B, is administered once in a dose that is between about 20 and about 100% of the MTD, to a human; and, if required, one or more (preferably two to seven) further doses each within the dose range mentioned above for the first dose are administered in further treatment cycles, preferably each dose after a period of time that allows for sufficient recovery of the treated individual from each preceding dose administration, especially more than two weeks after the preceding treatment, more especially two to 10 weeks, most especially three to six weeks after the preceding treatment, especially three weeks after that treatment.

More preferably, under (1) to (4) epothilone B is administered weekly to a human in a dose that lies between about 0.1 and about 6, preferably about 0.1 and about 5 mg/m$^2$, more preferably about 0.1 and about 3 mg/m$^2$, even more preferably about 0.1 and about 1.7 mg/m$^2$, most preferably about 0.3 and about 1 mg/m$^2$; or epothilone B is administered three-weekly (every 3 weeks) in a dose that is between about 0.3 and about 18 mg/m$^2$, preferably about 0.3 and about 15 mg/m$^2$, more preferably about 0.3 and about 12 mg/m$^2$, even more preferably about 0.3 and about 7.5 mg/m$^2$, still more preferably about 0.3 and about 5 mg/m$^2$, most preferably about 1.0 and about 3.0 mg/m$^2$. This dose is preferably administered to the human by intravenous (i.v.) administration during 2 to 120 min, more preferably during about 5 to about 30 min, most preferably during about 10 to about 30 min, e.g. during about 30 min.

More preferably, said treatment is repeated every about 1 to about 3 weeks, until disease progression, unacceptable toxicity, 1 or preferably 2 cycles beyond determination of a complete response, or patient withdrawal of consent for any reason is encountered.

(5) The present invention preferably also relates to an in vivo regimen for the treatment of a tumor disease, especially (i) of a tumor of the gastrointestinal tract, most especially a tumor of the colon and/or rectum (colorectal tumor); and/or (ii) a tumor of the genitourinary tract, especially a prostate tumor; especially where such tumor is refractory to treatment with an other chemotherapeutic, especially one of the taxane class, most especially TAXOL® (preferably a hormone-refractory prostate tumor); where epothilone A and/or B, especially epothilone B, is administered weekly to a warm-blooded animal in a dose that is below 80%, more preferably below 50% of the maximal tolerable dose (MTD).

Preferably, in the case of weekly treatment of a human with said epothilone(s), the dose is in the range of about 1 to about 60%, preferably about 10 to about 60%, e.g. about 5 to about 35% of the MTD, for example. in the range of about 30 to about 35% of the MTD. Preferably, for epothilone B the dose is in the range of about 5 to about 60%, preferably about 10 to about 60%, especially in the range of about 10 to about 45%, most especially in the range of about 30 to about 45% of the three-weekly MTD. of the three-weekly MTD. In a special case, the dose can be between about 2 and about 18 mg/m$^2$ for epothilone B.

More preferably, treatment is stopped after the third to eighth, especially after the third to fifth weekly administration followed by a rest period of two to five, e.g. two weeks before further treatment is resumed. Preferably and if required, in the case of weekly epothilone B administration treatment is stopped after the third to eighth administration followed by a rest period of two to four, e.g. two weeks before treatment is resumed by weekly administration.

(6) The invention preferably also relates to the in vivo treatment of a tumor disease by combined administration (a) of epothilone A and/or epothilone B, especially epothilone B, in combination with (b) an other chemotherapeutic agent selected from the group consisting of (A) alkylating agents, preferably cross-linking chemotherapeutics, preferably bis-alkylating agents,
(B) antitumor antibiotics, preferably doxorubicin (ADRIAMYCIN®, RUBEX®);
(C) antimetabolites;
(D) plant alkaloids;
(E) hormonal agents and antagonists;
(F) biological response modifiers, preferably lymphokines or interferons
(G) inhibitors of protein tyrosine kinases and/or serine/threonine kinases;
(H) antisense oligonucleotides or oligonucleotide derivatives; or
(I) miscellaneous agents or agents with other or unknown mechanism of action; the combined treatment being timed so that component (a) and (b) are combined for simultaneous or chronologically staggered use within a period of time which is small enough for the active compounds both of component (a) and of component (b) to mutually enhance antiproliferative activity, e.g. in a patient.

(7) The invention also relates to a product which comprises component (a) and component (b) as defined under (6) above, in the presence or absence of one or more pharmaceutically acceptable carrier materials, as a combination preparation for simultaneous or chronologically staggered administration to a human within a period of time which is small enough for the active compounds both of component (a) and of component (b) to mutually enhance activity against a tumor disease, especially (i) a tumor of the gastrointestinal tract, most especially a tumor of the colon and/or rectum (colorectal tumor); and/or (ii) a tumor of the genitourinary tract, especially a prostate tumor; especially where such tumor is refractory to treatment with an other chemotherapeutic, especially one of the taxane class, most especially TAXOL®; for treating said tumor disease.

Under (1) to (7) or the subsequent embodiments of the invention, administration of the epothilone, especially epothilone B, preferably takes place by infusion, especially by intravenous infusion.

The following are some especially preferred embodiments of the invention:

A1. The use of an epothilone, especially epothilone A and/or epothilone B, for the treatment of a proliferative disease that is refractory to treatment with other chemotherapeutics; or the use of said epothilone, especially epothilone B, for the manufacture of a pharmaceutical preparation for the treatment of a proliferative disease that is refractory to the treatment with other chemotherapeutics.

A2. The use according to A1 where the proliferative disease is a tumor disease that is refractory to a microtubule stabilizing agent of the taxane class, especially TAXOL®.

A3. The use according to any one of A1 to A2 where the proliferative disease is a colorectal tumor, and/or a metastasis thereof.

A4. The use according to any one of A1 to A2 where the proliferative disease is a prostatic tumor, and/or a metastasis thereof; especially a hormone-refractory prostate tumor.

B1. The use of an epothilone for the manufacture of a pharmaceutical preparation that is appropriate for administration of said epothilone once in a dose that is between about 1 and about 100% of the maximal tolerated dose (MTD) in a warm-blooded animal, to said warm-blooded animal for the treatment of a proliferative disease that is refractory to the treatment with other chemotherapeutics.

B2. The use according to B1 where the epothilone is epothilone A and/or epothilone B, preferably epothilone B.

B3. The use according to any one of B1 and B2 where the dose is between 25 and 100% of the maximal tolerated dose and the warm-blooded animal is a human.

B4. The use according to any one of B1 to B3 where the dose unit for an adult human is in the range of between about 0.3 and about 18, preferably about 0.3 and about 12, more preferably about 0.3 and about 7.5, most preferably about 1.0 and about 3 mg/m$^2$ of epothilone B with three-weekly treatment; or between about 0.1 and about 6, preferably about 0.1 to about 5, more preferably about 0.1 and about 3, most preferably about 0.3 and about 1 mg/m$^2$ for weekly treatment.

B5. The use according to any one of B1 to B4 where the dose is chosen so that after a period of time that allows for sufficient recovery of the treated individual from each preceding dose a further dose can be administered.

B6. The use according to any one of B1 to B5 where the proliferative disease is a tumor.

B7. The use according to any one of B1 to B6 where the proliferative disease is a colorectal tumor, and/or a metastasis thereof.

B8. The use according to any one of B1 to B6 where the proliferative disease is a prostate tumor, and/or a metastasis thereof.

B9. The use according to any one of B1 to B8 where the tumor is one that is refractory to treatment with a microtubule stabilizing agent of the taxane, microtubule stabilizing class of agents, especially TAXOL®.

C1. The use of an epothilone, preferably epothilone A and/or epothilone B, especially epothilone B, for the manufacture of a pharmaceutical preparation that is appropriate for administration of said epothilone once weekly, where the dose is 80% or less, preferably 50% or less, of the MTD.

D1. The use of an epothilone, especially epothilone A and/or epothilone B, for the manufacture of a pharmaceutical preparation that is appropriate for the combined administration (a) of an epothilone, preferably epothilone A and/or epothilone B, in combination with (b) another antitumor chemotherapeutic to a warm-blooded animal that suffers from a proliferative disease that is refractory to the treatment with other chemotherapeutics, especially a colorectal or prostate tumor and/or a metastasis thereof.

E1. A pharmaceutical preparation for the treatment of a proliferative disease, especially a tumor disease, especially one of those characterized as being preferred above or below, in a human, said preparation comprising an epothilone, especially epothilone B, in a dose ranging from 1 to 100%, preferably from 25 to 100% of the maximal tolerable dose (MTD), and a pharmaceutically acceptable carrier.

F1. A combination preparation comprising (a) epothilone A or preferably epothilone B and (b) one or more other antitumor chemotherapeutics, and a pharmaceutically acceptable carrier.

G1. A product which comprises as component (a) epothilone A and/or B, preferably epothilone B, and as component (b) any other antitumor chemotherapeutic, in the presence or absence of one or more pharmaceutically acceptable carrier materials, as a combination preparation for simultaneous or chronologically staggered administration to a warm-blooded animal, especially a human, within a period of time which is small enough for the active compounds both of component (a) and of component (b) to mutually enhance antitumor activity in said warm-blooded, animal, for treating a proliferative disease.

The invention relates most especially to the treatment of following tumor/cancer types with epothilone B:

(i) a gastrointestinal, especially a colorectal tumor that is refractory to a representative of the taxane class of anti-cancer agents, in particular TAXOL®; or more especially to the treatment with standard chemotherapy, especially with 5-fluorouracil, and/or TAXOL®.

(ii) a tumor of the genitourinary tract, especially a prostate tumor, including primary and especially metastatic tumors; more especially if refractory to hormone treatment;

(iii) an epidermoid, more especially epidermoid head and neck, most especially epidermoid mouth tumor, especially one of these that is refractory to treatment with an other chemotherapeutic, especially due to multi-drug resistance, especially to treatment with a member of the taxane class of anti-cancer agents, especially TAXOL®;

(iv) a lung tumor, especially a non-small cell lung cancer, that is refractory to treatment with an other chemotherapeutic, especially due to (mainly) multi-drug resistance, especially to treatment with a member of the taxane class of anti-cancer agents, especially TAXOL®; and/or (v) a breast tumor, especially a breast tumor that is multidrug resistant, more especially one that is refractory to treatment with a member of the taxane class of anti-cancer agents, especially TAXOL®.

Preferably, the invention relates to the treatment of any one of the above-mentioned tumor types (i) to (v), most preferably to that of (I), (ii), (iv) and (v).

More preferably, the invention relates to the treatment of any of the tumor types mentioned above under (i) to (v), especially to any one of them, by treatment with an intravenous infusion of epothilone B over 2 to 120 min, preferably during about 5 to about 30 min, more preferably during about 10 to about 30 min, most preferably during about 30 min;

said administration being repeated every one to three weeks, preferably every one week (weekly) or every three weeks;

where the epothilone B dose preferably is defined by formula 1, $$\text{single dose (mg/m}^2\text{)} = (0.1 \text{ to } y) \times N \qquad (I)$$

where N (a whole or fractional number) is the number of weeks between treatments that lies between about one and about three weeks, that is, N is about 1 to about 3; and y is 6, preferably 5, more preferably 4.

More preferably, the treatment dose is calculated according to the formula II $$\text{single dose (mg/m}^2\text{)} = (0.1 \text{ to } 2.5) \times N; \qquad (II);$$

even more preferably according to the formula III, $$\text{single dose (mg/m}^2\text{)} = (0.1 \text{ to } 1.7) \times N; \qquad (III);$$

or most preferably according to the formula IV $$\text{single dose (mg/m}^2\text{)} = (0.1 \text{ to } 1) \times N \qquad (IV)$$

where, in each of formulae II to IV, N corresponds to about 1 to about 3 (standing preferably for weekly up to three-weekly treatment).

More preferably, for weekly treatment the dose is between about 0.1 and about 6, preferably about 0.1 to about 5 mg/m$^2$, more preferably about 0.1 and about 3 mg/m$^2$, even more preferably about 0.1 and about 1.7 mg/m$^2$, most preferably about 0.3 and about 1 mg/m$^2$; or for three-weekly treatment between about 0.3 and about 18 mg/m$^2$, preferably about 0.3 and about 15 mg/m$^2$, more preferably about 0.3 and about 12 mg/m$^2$, even more preferably about 0.3 and about 7.5 mg/m$^2$, still more preferably about 0.3 and about 5 mg/m$^2$, most preferably about 1.0 and about 3.0 mg/m$^2$.

More preferably, rest periods of more than one week, more preferably of two to ten weeks, more preferably three to six weeks after the preceding treatment may be necessary (especially in the case of weekly treatment) after for example 3, 4, 6, 8, or more cycles, depending on patient condition, to allow for sufficient recovery from the preceding treatment.

Especially preferred are also treatment conditions and formulations in analogy to those mentioned in the Examples.

Pharmaceutical Formulations

The present invention also relates to the use of epothilone A and/or B, especially epothilone. A or preferably epothilone B, for the manufacture of a pharmaceutical formulation for use against a tumor disease as defined above; or to a pharmaceutical formulation for the treatment of said tumor disease comprising epothilone A and/or B, especially epothilone A or preferably epothilone B, and a pharmaceutically acceptable carrier.

The invention relates also to pharmaceutical compositions comprising epothilone A and/or epothilone B, especially epothilone B, for the treatment of a proliferative disease, especially a tumor disease defined as being preferred above, and to the preparation of pharmaceutical preparations for said treatment.

Epothilone A and/or B may be used, for example, for the preparation of pharmaceutical compositions that comprise an effective amount of the active ingredient together or in admixture with a significant amount of inorganic or organic, solid or liquid, pharmaceutically acceptable carriers.

The invention relates also to a pharmaceutical composition that is suitable for administration to a warm-blooded animal, especially a human, for the treatment of a proliferative disease as defined hereinbefore, comprising an amount of epothilone A and/or B, especially epothilone B, which is effective for the treatment of said proliferative disease, together with at least one pharmaceutically acceptable carrier.

The pharmaceutical compositions according to the invention are those for enteral, such as nasal, rectal or oral, or preferably parenteral, such as intramuscular or intravenous, administration to a warm-blooded animal (human or animal), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration; preferably, the dose is one of the preferred doses as defined above, being accomodated appropriately where pediatric treatment is intended.

The pharmaceutical compositions comprise from about 0.00002 to about 95%, especially (e.g. in the case of infusion dilutions that are ready for use) of 0.0001 to 0.02%, or (for example in case of infusion concentrates) from about 0.1% to about 95%, preferably from about 20% to about 90%, active ingredient (weight by weight, in each case). Pharmaceutical compositions according to the invention may be, for example, in unit dose form, such as in the form of ampoules, vials, suppositories, dragees, tablets or capsules.

Preferably, the dose is chosen so as to allow for the treatment regimen based on the MTD mentioned above for single or rare treatment of a tumor disease.

The pharmaceutical compositions of the present invention are prepared in a manner known per se, for example by means of conventional dissolving, lyophilizing, mixing, granulating or confectioning processes.

Solutions of the active ingredient, and also suspensions, and especially isotonic aqueous solutions or suspensions, are preferably used, it being possible, for example in the case of lyophilized compositions that comprise the active ingredient alone or together with a pharmaceutically acceptable carrier, for example mannitol, for such solutions or suspensions to be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection or infusion compositions are prepared in customary manner under sterile conditions; the same applies also to introducing the compositions into ampoules or vials and sealing the containers.

Preferred is an infusion formulation comprising epothilone A and/or epothilone B, especially epothilone B, and a pharmaceutically acceptable organic solvent.

The formulation does not require the use of a surfactant. Surfactants such as Cremophor may cause allergic reactions and they also can leach plasticizers from standard PVC containers, tubing and the like. Consequently, when they are employed one is required to use special infusion apparatus, e.g. nitro-glycerine tubing and non-plastizised containers, such as glass, tubing and the like.

The pharmaceutically acceptable organic solvent used in a formulation according to the invention may be chosen from any such organic solvent known in the art. Preferably the solvent is selected from alcohol, e.g. absolute ethanol or ethanol/water mixtures, more preferably 70% ethanol, polyethylene glycol 300, polyethylene glycol 400, polypropylene glycol or N-methylpyrrolidone, most preferably polypropylene glycol or 70% ethanol or especially polyethylene glycol 300.

The Epothilones may preferably be present in the formulation in a concentration of about 0.1 to about 100 mg/ml, more preferably about 1 to about 100 mg/ml, still more preferably about 1 to about 10 mg/ml (especially in infusion concentrates).

Epothilone A and Epothilone B may be used as pure substances or as a mixture of Epothilone A and B. Given the greater anti-tumour activity of Epothilone B it may be employed in a lower concentration than Epothilone A in the formulation. When used in its pure form it is preferable to employ a concentration of Epothilone A of 5 to 100 mg/ml, preferably 10 to 50 mg/ml, whereas when Epothilone B is used in its pure form it is preferably employed in a concentration of 0.1 to 10, more preferably 1 to 10, still more preferably 1 to 2 mg/ml (this number makes reference especially to an infusion concentrate that, before treatment, is diluted accordingly, see below).

Such formulations are conveniently stored in vials or ampoules. Typically the vials or ampoules are made from glass, e.g. borosilicate or soda-lime glass. The vials or ampoules may be of any volume conventional in the art, preferably they are of a size sufficient to accommodate 0.5 to 5 ml of formulation. The formulation is stable for periods of storage of up to 12 to 24 months at temperatures of at least 2 to 8° C.

Formulations must be diluted in an aqueous medium suitable for intravenous administration before the epothilone can be administered to a patient.

The infusion solution preferably must have the same or essentially the same osmotic pressure as body fluid. Accordingly, the aqueous medium preferably contains an isotonic agent which has the effect of rendering the osmotic pressure of the infusion solution the same or essentially the same as body fluid.

The isotonic agent may be selected from any of those known in the art, e.g. mannitol, dextrose, glucose and sodium chloride. Preferably the isotonic agent is glucose or sodium chloride. The isotonic agents may be used in amounts which impart to the infusion solution the same or essentially the same osmotic pressure as body fluid. The precise quantities needed can be determined by routine experimentation and will depend upon the composition of the infusion solution and the nature of the isotonic agent. Selection of a particular isotonic agent is made having regard to the properties of the active agent.

The concentration of isotonic agent in the aqueous medium will depend upon the nature of the particular isotonic agent used. When glucose is used it is preferably used in a concentration of from 1 to 5% w/v, more particularly 5% w/v. When the isotonic agent is sodium chloride it is preferably employed in amounts of up to 1% w/v, in particular 0.9% w/v.

The infusion formulation may be diluted with the aqueous medium. The amount of aqueous medium employed as a diluent is chosen according to the desired concentration of Epothilone in the infusion solution. Preferably the infusion solution is made by mixing a vial or ampoule of infusion concentrate afore-mentioned with an aqueous medium, making the volume up to between 20 ml and 200 ml, preferably between about 50 and about 100 ml, with the aqueous medium.

Infusion solutions may contain other excipients commonly employed in formulations to be administered intravenously. Excipients include antioxidants.

Antioxidants may be employed to protect the epothilone against oxidative degradation. Antioxidants may be chosen from any of those antioxidants known in the art and suitable for intravenous formulations. The amount of antioxidant may be determined by routine experimentation. As an alternative to the addition of an antioxidant, or in addition thereto, the antioxidant effect may be achieved by displacing oxygen (air) from contact with the infusion solution. This may be conveniently carried out by purging the container holding said infusion solution with an inert gas, e.g. nitrogen.

Infusion solutions may be prepared by mixing an ampoule or vial of the formulation with the aqueous medium, e.g. a 5% w/v glucose solution in WFI or especially 0.9% sodium chloride solution in a suitable container, e.g. an infusion bag or bottle.

The infusion solution, once formed, is preferably used immediately or within a short time of being formed, e.g. within 6 hours.

Containers for holding the infusion solutions may be chosen from any conventional container which is non-reactive with the infusion solution. Glass containers made from those glass types afore-mentioned are suitable although it may be preferred to use plastics containers, e.g. plastics infusion bags.

Plastics containers may be principally those composed of thermoplastic polymers. Plastics materials may additionally comprise additives, e.g. plastizisers, fillers, antioxidants, antistatics and other additives conventional in the art.

Plastics suitable for the present invention should be resistant to elevated temperatures required for thermal sterilisation. Preferred plastics infusion bags are those made from PVC plastics materials known in the art.

A wide range of container sizes may be employed. When selecting a container size, consideration may be paid to the solubility of the epothilone in the aqueous medium and the ease of handling and, if appropriate, storage of the container.

It is preferred to use containers which can accommodate between about 250 to 1000 ml of infusion solution, but preferably about 50 to about 120 ml.

Infusion solutions act in a similar fashion to infusion solutions of the microtubule interacting agent paclitaxel, and are beneficial in treating conditions for which paclitaxel might be used. For certain tumors epothilones offer enhanced beneficial effects compared with paclitaxel.

Dosage forms may be conveniently administered intravenously in a dosage of up to 100 mg/m$^2$ Epothilone A and up to about 18 mg/m$^2$ of Epothilone B. The exact dosage required and the duration of administration will depend upon the seriousness of the condition and the rate of administration, and it is preferably as defined above. As the dose may be delivered intravenously, the dose received and the blood concentration can be determined accurately on the basis of known in vivo and in vitro techniques.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable pharmaceutically acceptable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings; there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plastiziser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilizers. In soft capsules the active ingredient is preferably dissolved or suspended in suitable oily excipients, such as fatty oils, paraffin oil or liquid polyethylene glycols, and also stabilizers and/or antibacterial agents may be added. Dyes or pigments may be added to the tablets or dragëe coatings or the capsule casings, for example for identification purposes or to indicate different doses of active ingredient.

In the case of combinations with an other chemotherapeutic, a fixed combination of two or more components (a) and (b) as defined above or two or more independent formulations (e.g. in a kit of part) are prepared as described above, or the other chemotherapeutic(s) is/are used in standard formulations that are marketed and known to the person of skill in the art.

EXAMPLES

The following Examples are intended to illustrate the present invention but are not intended to limit the scope thereof. Especially the cell lines mentioned therein are not thought to limit the scope of the invention as they are merely representatives and may be replaced with different cell lines and tumor cells for which they are representatives.

Preparation of Compound Solutions

A stock solution of epothilone B at 10 mg/ml in DMSO is prepared and stored at −20° C. Aliquots are diluted in aqueous solutions to a final concentration of 5% v/v DMSO, 0.05% v/v Tween 80 (polyoxyethylen-sorbitan-monooleate; ICI Americas, Inc.), and 95% v/v physiological saline (0.9% w/v NaCl).

Cells and Cell Culture Conditions

Human colorectal adenocarcinoma cell line HCT-15 (ATCC CCL 225) is from the American Type Culture Collection (Rockville, Md., USA), and the cells are cultivated in vitro as recommended by the supplier. HCT-15 is an epithelial-like cell line. (Cancer Res. 39: 1020-25 [1979]) that is multi-drug resistant by virtue of over-expression of P-glycoprotein (P-gp, gp170, MDR-1;Anticancer Res. 11: 1309-12 [1991]; J. Biol. Chem. 264: 18031-40 [1989]; Int. J. Cancer 1991; 49: 696-703 [1991]) and glutathione-dependent resistance mechanisms (Int. J. Cancer 1991; 49: 688-95 [1991]).

The Colo 205 cell line is also a human colon carcinoma cell line (ATCC No. CCL 222; see also Cancer Res. 38, 1345-55 [1978] which was isolated from ascitic fluid of a patient, displays epithelial-like morphology and is generally considered to be drug-sensitive.

A human androgen-independent prostate cancer cell line is used to establish subcutaneous and orthotopic models in mice. The human metastatic prostate carcinoma PC-3M is obtained from Dr. I. J. Fidler (MD Anderson Cancer Center, Houston, Tex., USA) and is cultured in Ham's F12K media supplemented with 7% v/v FBS. The PC-3M cell line is the result of isolation from liver metastasis produced in nude mice subsequent to intrasplenic injection of PC-3 cells [ATCC CRL 1435; American Type Culture Collection (Rockville, Md., USA)], and they can grow in Eagle's MEM supplemented with 10% fetal bovine serum, sodium pyruvate, non-essential amino acids, L-glutamine, a two-fold vitamin solution (Gibco Laboratories, Long Island, N.Y.) and penicillin-streptomycin (Flow Laboratories, Rockville, Md.). The PC-3M cell line is hormone-insensitive (that is, it grows in the absence of androgens). The PC-3 cell line is androgen receptor negative, as is presumably the derived PC-3M cell line. PC-3 is a cell line available from ATCC (ATCC CRL 1435) and corresponds to a grade IV prostatic adenocarcinoma isolated from a 62-year-old Caucasian male; the cells exhibit low acid phosphatase and testosterone-5-α-reductase activity. The cells are near-triploid with a modal number of 62 chromosomes. No normal Y chromosomes can be detected by Q-band analysis.

Human lung adenocarcinoma A549 (ATCC CCL 185; isolated as explant culture from lung carcinoma tissue from a 58-year-old Caucasian male); shows epithelial morphology and can synthesize lecithin with a high percentage of desaturated fatty acids utilizing the cytidine diphosphocholine pathway; a subtelocentric marker chromosome involving chromosome 6 and the long arm of chromosome 1 is found in all metaphases. The human breast carcinoma ZR-75-1 (ATCC CRL 1500; isolated from a malignant ascitic effusion of a 63-year-old Caucasian female with infiltrating ductal carcinoma); is of mammary epithelial origin; the cells possess receptors for estrogen and other steroid hormones and have a hypertriploid chromosome number.

The human epidermal (mouth) carcinoma cell line KB-8511 (a P-gp over-expressing cell line derived from the epidermoid (mouth) KB-31 carcinoma cell line) is obtained from Dr. R. M. Baker, Roswell Park Memorial Institute (Buffalo, N.Y., USA) (for description see Akiyama et al., Somat. Cell. Mol. Genetics 11, 117-126 (1985) and Fojo A., et al., Cancer Res. 45, 3002-3007 (1985)) and is cultured as previously described (Meyer, T., et al., Int. J. Cancer 43 851-856 (1989)). KB-8511 cells, like KB-31, are derived from the KB cell line (ATCC) and they are human epidermal carcinoma cells; KB-31 cells can be grown in mono-layer using Dulbecco's modified Eagle's medium (D-MEM) with 10% fetal calf serum (M.A. Bioproducts), L-glutamine (Flow), penicillin (50 units/ml) and streptomycin (50 µg/ml (Flow); they then grow with a doubling time of 22 h, and their relative plating efficiency is approximately 60%. KS-8511 is a cell line derived from the KB-31 cell line by use of colchicine treatment cycles; it shows about a 40-fold relative resistance against colchicine when compared with the KB-31 cells; it can be grown under the same conditions as KB-31.

For more details on the characteristics of the cell lines, see the ATCC catalogue and references cited therein, or the other references cited above.

The following cell lines mentioned above have been deposited under the Budapest Treaty on Feb. 20, 1998, at the Deutsche Sammlung von Mikroorganismen und Zellkulturen GmbH (DSMZ, Mascheroder Weg 1b, D-38124 Braunschweig, Germany) under the following accession numbers, respectively: PC-3M: DSM ACC2338; A-549: DSM ACC2337; KB-8511: DSM ACC2342.

In addition, the following cell lines mentioned above have been deposited under the Budapest Treaty on Dec. 1, 1998, at the Deutsche Sammlung von Mikroorganismen und Zellkulturen GmbH (DSMZ, Mascheroder Weg 1b, D-38124 Braunschweig, Germany) under the following accession numbers, respectively: ZR -75-1: DSM ACC2376; HCT-15: ACC2377.

In the following, general methods are described for the tests made. Where specific conditions are mentioned, these prevail over the general descriptions presented in the next paragraphs:

Antiproliferative Assays:

Antiproliferative assays are performed as previously described (Int. J. Cancer 43, 851-6 (1989)). Briefly, cells are seeded at $1.5 \times 10^3$ cells/well into 96-well microtiter plates and incubated overnight. Compounds are added in serial dilutions on day 1. The plates are then incubated for an additional 2 to 5 days, allowing for at least one cell doubling (cell line dependent), after which the cells are fixed with 3.3% v/v glutaraldehyde, washed with water and stained with 0.05% w/v methylene blue. After washing, the dye is eluted with 3% v/v HCl and the optical density measured at 665 nm with a Spectra-Max 340 (Bucherer, Basel, Switzerland). IC50 values are determined by a computerized system (SoftPro, Bucherer, Basel, Switzerland) using the formula (OD test−OD start)/(OD control−OD start)×100. IC50 is defined as the drug concentration which leads to 50% of cells per well compared to control cultures (100%) at the end of incubation period.

In vivo Antitumor Activity Against s.c. Transplanted Tumors

Female or male BALB/c nu/nu (nude) mice are kept under sterile conditions (10 to 12 mice per Type III cage) with free access to food and water. Mice weigh between 20 and 25 grams at the time of tumor implantation. Tumors are established by subcutaneous injection of cells (minimum $2 \times 10^6$ cells in 100 μl PBS or medium) in carrier mice (4-8 mice per cell line). The resulting tumors are serially passaged for a minimum of three consecutive transplantations prior to start of treatment. Tumor fragments (approx. 25 mg) are implanted s.c. into the left flank of animals with a 13-gauge trocar needle while the mice are exposed to Forene (Abbott, Switzerland) anesthesia.

Tumor growth and body weights are monitored once or twice weekly. All treatments are administered intravenously (i.v.) and are initiated when a mean tumor volume of approximately 100 to 250 mm$^3$ is attained, depending upon the tumor type. Tumor volumes are determined using the formula (L×D×π)/6 (see Cancer Chemother. Pharmacol. 24:148-154, [1989]). Treatments with epothilone B vary the dose and the frequency of administration. Comparator agents are administered according to previously determined optimal treatment regimens. In addition to presenting changes in tumor volumes over the course of treatment, antitumor activity is expressed as T/C % (mean increase of tumor volumes of treated animals divided by the mean increase of tumor volumes of control animals multiplied by 100). Tumor. regression (%) represents the smallest mean tumor volume compared to the mean tumor volume at the start of treatment, according to the formula Regression (%)=(1−$V_{end}/V_{start}$)×100($V_{end}$=final mean tumor volume, $V_{start}$=mean tumor volume at the start of treatment. Any animals in which the tumor has reached a size exceeding approximately 1.5 to 2.5 cm$^3$ are sacrificed. Details can be found below.

In vivo Antitumor Activity Against Orthotopically Injected Cells

Human prostate carcinoma PC-3M cells ($1 \times 10^6$ cells per 20 μl phosphate buffered saline) are injected into the left ventricle of the prostate of each animal (n=6-9/group) according the method previously described (see Stephenson et al., J. Natl. Cancer Inst. 84, 951-7 (1992)). Treatment is started on day 14 after cell injection. At this time point a mean tumor weight of ~20 mg is established. Epothilone B is administered either once or once weekly. Mice are sacrificed 42 days post tumor inoculation, and the prostates are carefully removed, dissected free of adhering tissue and weighed. Mesengeal lymph nodes are examined for the presence of metastases, dissected free of adhering tissue and weighed. Mesenteric lymph nodes are examined for the presence of metastases, dissected free of adhering tissue and weighed.

Tumor weight and body weights are monitored once or twice weekly. All treatments are administered intravenously (i.v.) and are initiated 14 days post cell injection. Treatment with epothilone B varies the dose and frequency of administration. Antitumor activity is expressed as T/C % (mean tumor weight of treated animals divided by the mean tumor weight of control animals multiplied by 100).

Statistical Analyses

The basic strategy for statistical analyses is to use tests for multiple comparisons to judge the statistical significance of differences between treatment groups, and differences within a group (i.e. comparing to the start of treatment) to determine if treatment induces stable disease or tumor regressions. As subcutaneous tumor volumes are not normally distributed, differences in the subcutaneous tumor volumes between treatment groups are determined using the non-parametric Kruskal-Wallis one way ANOVA test on ranked data (Rank sum test), and the statistical significance of differences between treatment groups as compared to control groups determined using the Dunnett test. Pair-wise comparisons between all groups is performed using the Student-Newman-Keuls (SNK) method. Organ weights are not always normally distributed and are analyzed either using non-parametric tests (as above) or are transformed to normality (Log [organ weight]) and are analyzed by One-way ANOVA followed by the Dunnett test (comparisons to controls) or using Tukey (between group comparisons). Statistical analysis on Δ tumor volumes uses the Kruskal-Wallis one way ANOVA test on ranked data, comparing treatment groups with vehicle controls by Dunnett's test. Differences in the body weights between treatment groups with vehicle controls are analyzed by paired t-tests. Fisher's Exact Test is used to determine the significance of differences in mortalities between the groups. For all tests the level of significance is set at p<0.05, but note that for these small sample sizes, the desired power level of 0.8 is never obtained. For the orthotopic model, Fisher's exact test is used to determine whether the ratios of mice bearing metastases are different between treatment groups and controls. Any statistical calculations are performed using SigmaStat 2.0 (Jandel Scientific).

Material

Epothilone B is purified from cultures of the myxobacterium Sorangium cellulosum by Biopharmaceuticals Production and Development Department, Novartis Pharma, Basel, Switzerland. TAXOL® (paclitaxel formulated for clinical use) is purchased from Bristol Myers Squibb (USA), paclitaxel from Calbiochem (USA), and 5-fluorouracil (Fluorouracil®) is from Roche (Switzerland). Cell culture materials are from Integra BioSciences (Wallisellen, Switzerland). Liquid media, fetal bovine serum (FBS) and media additives are from Gibco/BRL (Basel, Switzerland). BALB/c nu/nu (nude) mice are from Bomholtgaard (Copenhagen, Denmark) or obtained from the Novartis Animal Farm (Sisseln, Switzerland). Normal BALB/c mice are from Iffa Credo (France) or obtained from Novartis Animal Farm (Sisseln, Switzerland).

Determination of the Maximal Tolerated Dose (MTD)

For the MTD determination, female BALB/c nude mice or BALB/c mice (obtained from Novartis Animal Farm, Sisseln, Switzerland) are treated once intravenously with epothilone B (n=3 per dose group). The dosage is increased (2, 4, 6, 8, 10 and 12 mg/kg) and the mice are observed for the presentation of overt toxic effects for 10 days after drug treatment.

Example 1

Determination of the Maximal Tolerated Dose (MTD)

The results from the maximal tolerated dose (MTD) study are presented in Table 1 and Table 2.

TABLE 1

Determination of the single i.v. dose MTD for
epothilone B in normal female BALB/c mice.

| Dose | Δ (p value) | % Change | Mortalities |
|---|---|---|---|
| | Body Weight (mean g ± SD) | | |
| | Experiment 1 | | |
| 12 | −5.4 ± 2.9 (p = 0.085) | −23.6 ± 11.9 | 3/3 |
| 10 | −5.6 ± 0.6 (p = 0.003) | −24.9 ± 1.6 | 3/3 |
| 8 | −5.1 ± 3.2 (p = 0.110) | −22.1 ± 13.1 | 3/3 |
| 6 | −6.1 ± 0.9 (p = 0.007) | −28.6 ± 3.5 | 1/3 |
| | Experiment 2 | | |
| 8 | −5.0 ± 1.0 (p = 0.013) | −25.3 ± 3.9 | 3/3 |
| 6 | −5.3 ± 0.6 (p = 0.004) | −27.5 ± 2.1 | 2/3 |
| 4 | 1.3 ± 0.6 (p = 0.057) | 6.5 ± 2.6 | 0/3 |
| 2 | 2.3 ± 0.6 (p = 0.02) | 12.3 ± 3.0 | 0/3 |

Epothilone B is given as a single i.v. bolus dose at 2, 4, 6, 8, 10 or 12 mg/kg. Survival and body weights of the mice are monitored daily. Changes (Δ) in body weights are determined comparing the last measured body weight to that before treatment.

TABLE 2

Determination of the single i.v. dose MTD for
epothilone B in female BALB/c nude mice.

| Dose | Δ (p value) | % Change | Mortalities |
|---|---|---|---|
| | Body Weight (mean g ± SD) | | |
| 12 | −5.1 ± 0.6 (p = 0.004) | −22.9 ± 3.1 | 3/3 |
| 10 | −5.6 ± 3.3 (p = 0.336) | −23.7 ± 13.6 | 1/3 |
| 8 | −3.8 ± 2.7 (p = 0.250) | −16.8 ± 12.2 | 1/3 |
| 6 | −1.0 ± 0.5 (p = 0.077) | −4.2 ± 2.1 | 0/3 |
| 4 | −0.4 ± 0.6 (p = 0.427) | −1.7 ± 2.9 | 0/3 |
| 2 | 1.0 ± 0.5 (p = 0.071) | 4.2 ± 2.1 | 0/3 |
| 0 | 0.6 ± 0.6 (p = 0.151) | 3.0 ± 2.9 | 0/3 |

Epothilone B is given as a single i.v. bolus dose at 2, 4, 6, 8, 10 or 12 mg/kg. Survival and body weights of the mice are monitored daily. Changes (Δ) in body weights are determined comparing the last measured body weight to that before treatment.
It follows from these experiments that in normal mice the MTD is around 4 mg/kg, while in nude mice the MTD is around 6 mg/kg.

Example 2

Toxicity of Epothilone B (Two-Week Intravenous Comparative Toxicity Study in Mice)

In order to assess the sub-chronic intravenous toxicity of epothilone B, a non-GLP two-week i.v. toxicity study in non-tumor bearing, normal female BALB/c mice is conducted, involving analysis of mortality, clinical signs, body weight, food consumption, hematology, clinical biochemistry, urinalysis, and organ weights as well as macro and microscopic examinations. The study is based on two different dosing regiments of epothilone B of 3 mg/kg and 10 mg/kg, respectively, administered on days 1 and 8 (8 animals per group). Half of the animals are killed on day 15 (main group) and necropsy is performed. For the other half (recovery group) a recovery period of 5 weeks is allowed after administration of the second dose before sacrifice and subsequent necropsy on day 43. However, for the 10 mg/kg dose all animals of the recovery group have to be sacrificed prematurely on day 19, due to poor general condition.

No mortalities occur throughout the treatment period at either dose level (days 1-14) and for the 3 mg/kg dose group all animals of the recovery group survive until the end of the study. Body weight loss is observed for all animals in the 10 m/kg dose group during the first and second week, whereas body weight loss at the 3 mg/kg dose is only apparent in the second week. Body weight development during the recovery period is similar for treated and control animals.

Both dose levels of epothilone B induce a reduction in the number of leukocytes, especially of neutrophils and lymphocytes, in all treated animals (day 15), but the effect is more pronounced at the 10 mg/kg dose. In addition, slight increases in basophil counts as well as decreased levels of monocytes are observed in some individual animals at both dose levels. Slightly lower values for red blood cell parameters with increases in reticulocytes and platelets are recorded only for the 10 mg/kg dose. At the end of the recovery period (day 43) hematological parameters are normal for two out of the four animals of the 3 mg/kg dose recovery group, whereas the other two still suffer from reduced white blood cell counts.

Only minor changes are observed in the clinical chemistry profile of treated animals, which cannot be clearly related to treatment with epothilone B.

Treatment with epothilone B at both dose levels leads to pronounced changes in thymus, spleen, and uterus weights (day 15). In addition, slight reductions in liver weight are observed. (Organ weight is determined for adrenal glands, liver, thymus, spleen, brain, ovaries, kidneys, uterus, and heart). For the 3 mg/kg dose, organ weights at the end of the recovery period (day 43) are comparable to those of control animals, indicating full recovery. (No organ weights are taken for the sacrificed animals of the 10 mg/kg dose recovery group).

Microscopic investigation of histologically processed selected tissues from animals sacrificed on day 15 reveals moderate to marked atrophy of the thymus for the 3 mg/kg and the 10 mg/kg dose, respectively. In addition, minimal lymphoid atrophy in the spleen, minimal to slight myeloid hypoplasia in the sternal bone marrow, and minimally increased hemopoiesis in the spleen are observed at 10 mg/kg dose. At 3 mg/kg the sternal bone marrow shows minimal to slight erythroid and myeloid atrophy. Minimal single cell necrosis is noted in the intestinal mucosa (small and large intestine) at both dose levels, but with a higher incidence at the 10 mg/kg dose.

Animals from the recovery groups at both dose levels show slight myeloid hyperplasia and/or athropy in the bone marrow. At 10 mg/kg slight lymphoid atrophy is also seen in the spleen and in addition slight to moderate hemosiderosis is present. There is no thymic tissue available for microscopic examination at 10 mg/kg, indicating that thymus atrophy might also have been present in these mice. No histological alterations in the thymus are found on day 43 for the animals from the 3 mg/kg dose recovery group.

In conclusion, at a dose level of 3 mg/kg (dosing on days 1 and 8) epothilone B is tolerated without mortality for the total observation period of 43 days, while animals dosed with 10 mg/kg have to be sacrificed on day 19, due to poor health condition. Body weight loss occurs at both dose levels during the treatment period. Hematology reveals lower values for leukocytes, neutrophils and lymphocytes with higher basophil and lower monocyte counts for some individual mice in both dose groups. In addition, evidence of anemia is seen at both dose levels. No effects on clinical chemistry profile are observed. Moderate to marked atrophy of the thymus are observed at 3 and 10 mg/kg after the treatment period only (day 15), together with minimal lymphoid atrophy in the spleen at the 10 mg/kg dose. In addition, myeloid hypoplasia in bone marrow and increased hemopoiesis in the spleen are detectable at 10 mg/kg. Slight erythroid and myeloid atrophy of bone marrow is seen at 3mg/kg. Single cell necrosis is detected in the intestinal mucosa at 3 and 10 mg/kg at the end of the treatment period only.

Conclusions

The most important conclusions emerging from the data summarized in Examples 1 and 2 for the toxicological findings with epothilone B can be summarized as follows:

The MTD for single dose i.v. administration of epothilone B to normal and nude mice from a BALB/c background corresponds to 4 mg/kg and 6 mg/kg, respectively. Nude mice thus are less sensitive to the toxic effects of the compound than normal mice.

In normal mice, two doses of 3 mg/kg given one week apart are reasonably well tolerated and do not cause mortality up to day 43 after the initial dose. The same dosing regimen at a 10 mg/kg dose level results in death (or sacrifice) of all treated animals.

Example 3

In vitro Activity of Epothilones Against Cell Lines

The potent anti-proliferative activity of epothilone B is confirmed for some human cancer cell lines; the results of these experiments are summarized in Table 3. Epothilone B generally exhibits higher potency than paclitaxel, particularly against cancer cells with a multidrug resistant (MDR) phenotype (e.g. KB-8511, HCT-15).

TABLE 3

In vitro activity of the epothilones against human carcinoma cell lines. IC50-values [nM] for growth inhibition of human carcinoma cell lines by epothilone B in comparison to paclitaxel (5 d exposure, mean ± SD, n = 3). Values in parenthesis indicate relative resistance, i.e., IC50 (resistant line)/IC50 (parental line).

| Cell Line | epothilone B | paclitaxel |
|---|---|---|
| A549 (Lung) | $0.19 \pm 0.12^a$ | $3.75 \pm 0.92$ |
| ZR-75-1 (Breast) | $0.64 \pm 0.42$ | $3.60 \pm 1.87$ |
| HCT-15 (Colon) | $0.41 \pm 0.15$ | $106 \pm 54$ |
| KB-8511 | $0.89 \pm 0.47^b$ | $994 \pm 281^b$ |
| (Epidermoid, MDR) | (1.25) | $(343)^a$ |
| PC-3M (Prostate) | $3.82 \pm 0.47^c$ | $6.74 \pm 0.72^c$ |

[a] Mean ± SD, n = 2.
[b] 2 d Exposure;
[c] 3 d exposure
MDR = Multidrug Resistant Example 4

Antitumor Activity of the Epothilones Against Human Colorectal Adenocarcinoma HCT-15 Tumors Tumor volumes are used as the primary indicator of activity of antitumor agents used alone or in combination, and changes in body weights are measured as an indicator of treatment tolerability.

As can be deduced from Table 4, a single 4 mg/kg dose of epothilone B is able to produce tumor regressions (p<0.05 vs. vehicle controls; Dunnett's) in drug-resistant, P-gp over-expressing, HCT-15 colon tumors (FIG. 1 and Table 1). This activity is clearly superior to five 20 mg/kg administrations of TAXOL® or two 75 mg/kg 5-fluorouracil administrations (p<0.05 vs. epothilone B; SNK test). HCT-15 tumors are resistant to both TAXOL® and 5-fluorouracil, in that final T/C values of 50% and 88%, respectively, are obtained (both p>0.05 vs. controls; Dunnett's). Epothilone B treatment is well tolerated in that body weight is stable under treatment; vehicle-treated mice gain weight. No mortalities due to treatment are observed with epothilone B. In contrast, some mortalities are observed with TAXOL® treatment (⅛ [12.5%] deaths) and a greater extent of lethality occurs with 5-fluorouracil (⅘ [50%] deaths); however, due to the small size of the treatment groups, this does not reach statistical significance (p>0.05 vs. controls; Fisher's Exact Test). Mice surviving either treatment demonstrate stable body weights.

This result indicates epothilone B produces a pronounced anti-tumor effect against HCT-15 tumors resistant to TAXOL® and 5-fluorouracil and is well-tolerated at this 4 mg/kg dose.

TABLE 4

Antitumor effect of epothilone B in comparison with TAXOL ® or 5-fluorouracil against subcutaneously transplanted human HCT-15 colon carcinoma in female BALB/c nude mice.

| | | Tumor Response | | | Host Response | | |
|---|---|---|---|---|---|---|---|
| Compound | Dose, Route, Schedule | T/C | Regression | D Tumor Volume (mm³) | D Body Weight (g) | % Body Weight Change | Survival (No. alive/total) |
| Vehicle controls | 25 ml/kg, i.v. days 14, | 100% | none | 1939 ± 333 | 2.1 ± 0.5 (p = 0.003) | 10 ± 2 | 8/8 |

TABLE 4-continued

Antitumor effect of epothilone B in comparison with TAXOL ® or 5-fluorouracil against subcutaneously transplanted human HCT-15 colon carcinoma in female BALB/c nude mice.

| Compound | Dose, Route, Schedule | Tumor Response | | | Host Response | | | |
|---|---|---|---|---|---|---|---|---|
| | | T/C | Regression | D Tumor Volume (mm³) | D Body Weight (g) | % Body Weight Change | Survival (No. alive/total) | |
| epothilone B | 16, 18, 20 and 22 4 mg/kg, i.v. once on day 14 | Regression | −61% | −97 ± 25 (p < 0.05) | 0.4 ± 0.3 (ns) | 2 ± 2 | 8/8 | |
| 5-fluorouracil | 75 mg/kg, i.v., on days 14 and 21 | 88% | none | 1654 ± 824 (ns) | 2.0 ± 0.7 (ns) | 9 ± 4 | 4/8 | |
| TAXOL ® | 20 mg/kg, i.v. days 14, 16, 18, 20 and 22 | 50% | none | 963 ± 298 (ns) | 0.7 ± 0.6 (ns) | 3 ± 3 | 7/8 | |

Tumor fragments of approximately 25 mg are implanted into the left flank of each female nude mouse (n = 8 per group).
Treatments are started on day 14 after tumor transplantation.
Epothilone B is administered once at 4 mg/kg, i.v. on day 14.
5-Fluorouracil is administered at 75 mg/kg, i.v., on days 14 and 21.
TAXOL ® is administered i.v. at 20 mg/kg/day, every second day for 5 treatments (days 14, 16, 18, 20 and 22).
Antitumor activity is expressed as T/C % (mean increase of tumor volumes of treated animals divided by the mean increase of tumor volumes of control animals multiplied by 100).
Tumor regression (%) represents the final mean tumor volume compares to the mean tumor volume at the start of treatment.
Δ Tumor volumes represent the tumor volume on the last treatment day minus the tumor volume on the first treatment day.
Statistical analyses on Δ tumor volumes uses Dunnett's test to compare treatment groups to controls.
Statistical analyses on body weight changes uses paired t-tests comparing body weights before treatment to those at the end of treatment; mice weigh ~20-25 g at the start of treatment.
Not significant is indicated by the abbreviation "ns".
Data presented are means ± SEM from animals surviving to the end of the experiment.

Example 5

Antitumor Effect of Epothilone B in Comparison With TAXOL® Against Subcutaneously Transplanted Human KB-8511 Epidermoid Carcinoma in Female BALB/c Nude Mice As can be deduced from Table 5, various regimens of epothilone B are able to inhibit the growth of TAXOL®-resistant KB-8511 tumors in nude mice. A single administration of 4 mg/kg epothilone B produces a transient regression (−51% on day 25 post transplantation; p<0.05 vs. vehicle controls, Dunnett), but the tumors re-grows by day 40 post-treatment to result in a final T/C of 24% (p<0.05 vs. vehicle controls, Dunnett). This single epothilone B administration is well tolerated producing stable body weights, and no mortalities occur.

Once weekly intravenous administration of epothilone B results in dose-dependent inhibition of tumor growth: 4 mg/kg produces 98% regressions (p<0.05 vs. vehicle controls; Dunnett); 2 mg/kg, produces transient 44% regressions and a final T/C of 14% (both p<0.05 vs. vehicle controls; Dunnett); 1 mg/kg produces a final T/C 81% (p >0.05 vs. vehicle controls; Dunnett). TAXOL® is inactive against KB-8511 tumors (T/C 132%, p>0.05 vs. vehicle controls; Dunnett). At the end of the experiment, ⅝ mice treated with 4 mg/kg/week, and ⅛ mice treated with 2 mg/kg/week epothilone B have undetectable tumors. Although 4 mg/kg once per week tend to reduce body weights (−5±7%), this does not reach statistical significance. Vehicle controls, 2 and 1 mg/kg/week epothilone B, and TAXOL® groups all display increasing body weights, and there are no mortalities, suggesting well-tolerated treatments.

These results indicate that epothilone B is effective against experimental epidermoid tumors that are TAXOL®-resistant.

TABLE 5

Antitumor effect of epothilone B in comparison with TAXOL ®
against subcutaneously transplanted human KB-8511
epidermoid carcinoma in female BALB/c nude mice.

| Compound | Dose, Route, Schedule | Tumor Response T/C | Tumor Response Regression | D Tumor Volume (mm³) | Host Response D Body Weight (g) | Host Response % Body Weight Change | Host Response Survival (No. alive/total) |
|---|---|---|---|---|---|---|---|
| Vehicle controls | 25 ml/kg, i.v. once per week | 100% | none | 2001 ± 405 | 2.6 ± 0.3 ($p < 0.001$) | 12 ± 2 | 8/8 |
| epothilone B | 4 mg/kg, i.v. once on day 13 | 24% | −51% (transient) | 484 ± 103 ($p < 0.05$) | 0.6 ± 0.6 (ns) | 3 ± 2 | 8/8 |
| epothilone B | 4 mg/kg, i.v. once per week | Regression | −98% | −107 ± 14 ($p < 0.05$) | −1.1 ± 0.4 (ns) | −5 ± 3 | 8/8 |
| epothilone B | 2 mg/kg, i.v. once per week | 14% | −44% (transient) | 289 ± 204 ($p < 0.05$) | 1.1 ± 0.4 ($p = 0.031$) | 5 ± 2 | 8/8 |
| epothilone B | 1 mg/kg, i.v. once per week | 81% | none | 1620 ± 290 (ns) | 2.6 ± 0.3 ($p = 0.008$) | 12 ± 1 | 8/8 |
| TAXOL ® | 20 mg/kg i.v. days 13, 15, 17, 19 and 21 | 132% | none | 2662 ± 509 (ns) | 3.3 ± 0.6 ($p < 0.001$) | 15 ± 3 | 8/8 |

Tumor fragments of approximately 25 mg are implanted into the left flank of each female nude mouse (n = 8 per group).
Treatments are started on day 13 after tumor transplantation.
epothilone B is administered once at 4 mg/kg; i.v. on day 13, or once per week at 4, 2 or 1 mg/kg, i.v., (on days 13, 21 and 27).
TAXOL ® is administered i.v. at 20 mg/kg/day, every second day for 5 treatments (days 13, 15, 17, 19 and 21).
Antitumor activity is expressed as T/C % (mean increase of tumor volumes of treated animals divided by the mean increase of tumor volumes of control animals multiplied by 100).
Tumor regression (%) represents the final mean tumor volume compared to the mean tumor volume at the start of treatment.
Changes (Δ) in Tumor volumes represent the tumor volume on the last treatment day minus the tumor volume on the first treatment day.
Statistical analyses on Δ tumor volumes uses Dunnett's test to compare treatment groups to controls.
Statistical analyses on body weight changes use paired t-tests comparing body weights before treatment to those at the end of treatment; mice weigh ~20-25 g at the start of treatment.
Not significant is indicated by the abbreviation "ns".
Data presented are means ± SEM from animals surviving to the end of the experiment.
It follows from the experiment that, while TAXOL ® is not effective, epothilone B treatment shows effective antitumor activity; even regression can be found at the 4 mg/kg dose.

Example 6

Antitumor Activity of the Epothilones Against Orthotopically Injected PC-3M Prostate Cells The results determining the activity of epothilone B against PC-3M tumors initially growing in prostate and then forming metastases in mesengeal lymph nodes are presented in Table 6.

In this experimental prostate cancer model, PC-3M cells initially grow in the prostate and then form metastases in mesenteric lymph nodes. Organ weights are used to assess antitumor activity of the treatments.

Table 6 represents the progress of the experimental cancer from 14 days post cell injection (start of treatment), where no lymph node involvement is observed, to 42 days post cell injection, where prostate and mesenteric lymph nodes dramatically increase in weight. All administration regimens of epothilone B are highly effective (all p<0.05 versus controls; Dunnett's test on log transformed data) in reducing prostate weights and preventing metastases of the tumor to the mesenteric lymph nodes. All of the active treatments are equivalent in antitumor activity (p>0.05; Dunn's). In each of the epothilone B treatment groups, only one animal has detectable metastases, as compared to all animals in the vehicle-treated controls (p<0.05; Fisher's Exact test), indicating that treatment with epothilone B significantly impairs the formation of detectable metastases.

Epothilone B treatments are not well-tolerated at the higher doses. Whereas a single administration of 6 mg/kg, or two administrations of 4 mg/kg, only tend to reduce body weights, administration of 8 mg/kg once, or 5 mg/kg once weekly, produces significant losses in body weight (Table 6). Treatment appears to promote survival of tumor-bearing mice; however, likely owing to the small numbers per treatment group, this only reaches statistical significance with the 6 mg/kg (once) regimen (p=0.029, Fisher's Exact test on final survival numbers).

Epothilone B demonstrates excellent antitumor activity in this model, both in terms of reduction of primary tumors and prevention of metastases. However, epothilone B, in some regimens, is poorly tolerated.

The results of this study indicate that epothilone B is active against human prostate carcinomas both in vitro and in vivo (see Example 3). Epothilone B is able to reduce the growth of the primary tumor and potently inhibit the formation of detectable metastases in an orthotopic model of prostate cancer. Furthermore, it may also promote survival of these tumor-bearing mice, although this needs to be examined in additional experiments. In parallel with its potent antitumor activity, epothilone B treatment produces significant body weight losses with the tested dosage regimens. However, the reasons for this poor tolerability are unknown.

The activity of epothilone B in the orthotopic PC-3M model is especially noteworthy. Orthotopic models are designed to implant the tumor within the tissues where the primary tumor is located in humans, and unlike most subcutaneous tumor implantation models, metastases frequently arise. Therefore, the repression of primary tumor growth in the prostate by epothilone B, and the inhibition of the formation and/or growth of mesenteric lymph node metastases represents a significant activity of epothilone B.

In summary, owing to potent antitumor activity in experimental prostate cancer models, which are considered relatively resistant to chemotherapy (Br. J. Cancer 75, 1593-600 (1997)), epothilone B appears to be a promising agent for the treatment of prostate cancer.

Example 7

Effect of Epothilone B Against Human Non-Small Cell Lung Carcinoma A549

3-10 million cells are implanted s.c. into the right axillary (lateral) region of outbred athymic (nu/nu) mice, and are allowed to grow until a tumor volume of approximately 100 mm$^3$ is established. Epothilone B is formulated in 1% DMSO in 5% glucose in distilled water (D5W), and administered i.v. either once only, once per week, 3 times per week, or 5 times per week. Positive controls are carried out with clinical formulations of TAXOL® diluted 6 fold with D5W and administered i.v. 3×/week.

Antitumor activity is expressed as % T/C (comparing Δ tumor volumes for treatment group to vehicle control group) at the end of the experiment. Regressions are calculated using the formula: $-(T/T_0-1)\times 100\%$, where T is the tumor volume for the treatment group at the end of the experiment, and $T_0$ is the tumor volume at the beginning of the experiment. Statistical significance is evaluated using a one-tailed Student's t-test.

Results: Table 7 summarizes results for A549 tumors. Epothilone B induces significant tumor inhibition (T/C=41%), with no detectable toxicity, when administered once at 6 mg/kg. A dose of 4 mg/kg administered 1×/week (4 mg/week) induces tumor stasis (T/C=7%), but also produces a 13% body weight loss. By comparison, at the dose of 1.5 mg/kg administered 3×/week (4.5 mg/week) all animals have

TABLE 6

Antitumor effect of epothilone B against orthotopically injected human PC-3M prostate carcinoma cells in male BALB/c nude mice.

| Compound | Dose, Route Schedule | Tumor Response (T/C %) Prostate | Lymph Nodes | Δ Body Weight (g) | % Body Weight Change | Host Response Survival (No. alive/total) |
|---|---|---|---|---|---|---|
| Vehicle controls | 25 ml/kg, i.v. once | 100% | 100% | −1.6 ± 1.8 (ns) | −5 ± 9 | 4/9 |
| Epothilone B | 8 mg/kg, i.v. once | 1 | 4 | −5.2 ± 4.3 (p = 0.009) | −13 ± 15 | 7/9 |
| | 6 mg/kg, i.v. once | 5 | 4 | −1.4 ± 4.1 (ns) | −6 ± 12 | 9/9 |
| | 5 mg/kg, i.v. once per week | 1 | 4 | −6.8 ± 1.5 (p < 0.001) | −25 ± 5 | 7/9 |
| | 4 mg/kg, i.v. once per week | 2 | 4 | −1.2 ± 2.3 (ns) | −1 ± 5 | 8/9 |

1 × 10$^6$ PC-3M cells in 20 μL of PBS are injected into the left ventricle of the prostate of each male nude mouse (n = 9 per group).
Treatments are started on day 14 after tumor cell injection.
epothilone B is administered i.v., once at 6 or 8 mg/kg, or once per week at 4 or 5 mg/kg.
Antitumor activity is expressed as T/C % (mean tumor weight of treated animals divided by the mean of tumor weight of control animals multiplied by 100).
Differences in body weights consider only animals surviving to the end of the experiment (day 42).
Statistical analyses on Δ body weight uses paired t-tests comparing body weights before treatment to the end of treatment; mice weigh ~20-25 g at the start of treatment.
Not significant is indicated by the abbreviation "ns".

to be euthanatized in the first week of the experiment due to toxicity. Dosing with 0.5 mg/kg, 5×/week (2.5 mg/week) induces tumor inhibition identical to that of the once only regimen (T/C=41%), but apparent cumulative toxicity results in a 23% body weight loss. TAXOL®, administered 3×/week at a dose of 20 mg/kg, does not inhibit tumor growth, and induces a 16% body weight loss, with lethality in 1 of 8 mice.

dependent inhibition of tumor growth, approaching tumor stasis at highest concentrations of the drug. Epothilone B produces marked inhibition of tumor growth at 3.5, and 3 mg/kg (T/C=15%, and 23%, respectively). Both doses cause comparable, but reversible (see Table 8) body weight loss of approximately 15%. The 2, and 1 mg/kg doses produced 43%, and 74% T/C, that are statistically significant, with no

TABLE 7

Antitumor activity of Epothilone B, compared to TAXOL ®, on A549 non small cell lung tumors in nude mice.

| Compound | Regimen | Dose (mg/kg) | Delta Mean Tumor Vol. (mm³) | % T/C | % Regression | Delta % Body Weight | Dead/ Total |
|---|---|---|---|---|---|---|---|
| 1% DMSO/ D5W | 3×/week | — | 439 | — | none | +8.9 | 0/7 |
| epothilone B | 5×/week | 0.5 | 178 | 41** | none | −23.1 | 0/8 |
| epothilone B | 3×/week | 1.5 | NE | NE | NE | NE | 8/8 |
| epothilone B | 1×/weeks | 4 | 32 | 7** | none | −13.2 | 0/8 |
| epothilone B | Once | 6 | 178 | 41** | none | +8.5 | 0/8 |
| TAXOL ® | 3×/week | 20 | 459 | 105 | none | −16.0 | 1/8 |
| Cremophor ®/ ethanol/ D5W | — | — | 207 | | | | |

Treatments are started on day 16 post implantation (10 million cells/animal).
Epothilone B is administered i.v. once at 6 mg/kg (day 16), once weekly at 4 mg/kg (days 16, 23, and 30), three times per week at 1.5 mg/kg (days 16, 18, 21, 23, 25, 28, 30, 32, and 35), or five times per week at 0.5 mg/kg (days 16-18, 21-25, 28-32, and 35-36).
TAXOL ® is administered i.v. three times per week at 20 mg/kg (days 16, 18, 21, 23, 25, 28, 30, 32, and 35) as split doses of 10 mg/kg given one hour apart.
Vehicle control (1% DMSO/D5W) is administered i.v. three times per week (days 16, 18, 21, 23, 25, 28, 30, 32, and 35).
All final data are recorded on day 37.
A single asterisk (*) indicates p < 0.05, and a double asterisk (**) indicates p < 0.01, using a one-tailed Student's t-Test.
"NE": not evaluable
— animals euthanatized due to compound toxicity.

Example 8

Antitumor Activity of Epothilone B Compared to TAXOL® on A549 Non-Small Cell Lung Tumors in Nude Mice Materials and methods pertaining to the human tumor xenograft model are as previously described. 10 or 1 million cells (A549) are implanted s.c. into the right axillary (lateral) region of outbred athymic (nu/nu) mice, and are allowed to grow until a mass of approximately 100 mm³ is established. Epothilone B is formulated in 1% DMSO in 5% glucose in distilled water (D5W), and administered i.v. once weekly for 3 weeks. Positive controls are carried out with clinical formulations of TAXOL® diluted 4 fold with D5W and administered i.v. 3×/week, for 3 weeks, in split doses (2×10 mg/kg) given 1 hour apart.

Antitumor activity is expressed as % T/C (comparing Δ tumor volumes for treatment group to vehicle control group) at the end of the experiment. Regressions are calculated using the formula: $(T/T_0-1)\times 100\%$, where T is the tumor volume for the treatment group at the end of the experiment, and $T_0$ is the tumor volume at the beginning of the experiment. Measurements are taken for an additional 2 weeks after completion of the regular 3 weeks experiments, to evaluate reversibility of drug-induced body weight loss, and sustainability of antitumor effects. Statistical significance is evaluated using a one-tailed Student's t-test, and Dunnett's, or Dunn's tests.

Results Table 8 summarizes results for A549 tumors, for the standard 3 weeks experiment. Once weekly administration of epothilone B produces statistically significant, dose body weight gain at 2 mg/kg, and normal body weight gain at 1 mg/kg. TAXOL®, administered 3×/week at a split dose of 2×10 mg/kg, does not inhibit tumor growth, but produces a 19% body weight loss.

TABLE 8

Antitumor activity of epothilone B, compared to TAXOL ®, on A549 non-small cell lung tumors in nude mice.

| Compound | Dose (mg/kg) | Delta Mean Tumor Vol. (mm³ ± SEM) | % T/C | Delta % Body Weight | Dead/ Total |
|---|---|---|---|---|---|
| 1% DMSO/ D5W | — | 262 ± 26 | — | +7.7 | 0/8 |
| Epothilone B | 1 | 195 ± 21 | 74*,** | +10.8 | 0/8 |
| Epothilone B | 2 | 113 ± 21 | 43*,** | +0.9 | 0/8 |
| Epothilone B | 3 | 60 ± 22 | 23*,** | −16.4 | 0/8 |
| Epothilone B | 3.5 | 40 ± 15 | 15*,** | −14.6 | 0/8 |
| Cremophor ®/ ethanol/D5W | — | 207 ± 26 | — | +8.3 | 0/8 |
| TAXOL ® | 20 | 293 ± 56 | 142 | −19.1 | 0/8 |

Treatments are started on day 13 post implantation (10 million cells/animal).
Epothilone B is administered i.v. once weekly for 3 weeks (days 13, 20, and 27) at doses of 1, 2, 3, and 3.5 mg/kg.
TAXOL ® is administered i.v. three times per week for 3 weeks at 20 mg/kg (days 14, 17, 19, 21, 24, 26, 28, 31, and 33) as split doses of 10 mg/kg given one hour apart.
Final data are recorded on day 34.
A single asterisk (*) indicates p < 0.05 using a one-tailed Student's t-Test, and a double asterisk (**) indicates p < 0.05 using a Dunnett's or Dunn's test.
Measurements are taken for an additional 2 weeks after completion of the regular 3 weeks experiments, and the final data for week 5 are summarized in Table 9. The antitumor effect remains unchanged, while animal body weights have recovered.
T/C values for the 3.5, 3, 2, and 1 mg/kg dose levels of epothilone B are 12%, 16%, 49% and 72%, respectively, and all groups have normal weight gain. TAXOL ® remains ineffective, and animals show only a 2% weight gain.

TABLE 9

Antitumor activity of epothilone B, compared to TAXOL ®, on A549 non small cell lung tumors in nude mice (extended observation).

| Compound | Dose (mg/kg) | Delta Mean Tumor Vol. (mm³ ± SEM) | % T/C | Delta % Body Weight | Dead/Total |
|---|---|---|---|---|---|
| 1% DMSO/D5W | — | 472 ± 81 | — | +11.8 | 0/8 |
| Epothilone B | 1 | 339 ± 24 | 72 | +12.6 | 0/8 |
| Epothilone B | 2 | 232 ± 39 | 49* | +13.5 | 0/8 |
| Epothilone B | 3 | 75 ± 25 | 16*,** | +13.2 | 0/8 |
| Epothilone B | 3.5 | 58 ± 25 | 12*,** | +9.7 | 0/8 |
| Cremophor ®/ethanol/D5W | — | 355 ± 80 | — | +13.0 | 0/8 |
| TAXOL ® | 20 | 509 ± 123 | 144 | +1.7 | 0/8 |

Measurements for the experiment described in Table 1 are extended by additional two weeks. Final data are recorded on day 48.
A single asterisk (*) indicates p < 0.05 using a one-tailed Student's t-Test, and a double asterisk (**) indicates p < 0.05 using a Dunnett's or Dunn's test.

Example 9

Antitumor Effect of Epothilone B on ZR-75-1 Breast Tumors

Table 10 shows the results of an experiment where the effect of TAXOL® and epothilone B on the breast cancer cell line ZR-75-1 are compared. The methods that are used for this tumor model have been described above.

It follows from the data that (judged on antitumor efficiency) the best dosing schedule is one where 4 mg/kg are administered weekly. However, mortality is observed at all dosages, suggesting that the ZR-75-1 tumor may affect the overall health of the mice in contrast to other tumor types.

TABLE 10

Antitumor effect of epothilone B against subcutaneously transplanted human estrogen-dependent ZR-75-1 breast tumors in female BALB/c nude mice.

| Compound | Dose, Route, Schedule | Tumor Response | | | Host Response | | |
|---|---|---|---|---|---|---|---|
| | | T/C (%) | Regression | Δ Tumor Volume (mm³) | Δ Body Weight (g) | % Body Weight Change | Survival (No. alive/total) |
| Vehicle controls | 25 ml/kg, i.v. every 7 days | 100 | none | 444 ± 58 | 0.9 ± 0.4 | 4 ± 2 | 6/6 |
| Epothilone B | 4 mg/kg, i.v. every 14 days | 46 | none | 208 ± 86 | −1.6 ± 1.1 | −7 ± 5 | 4/6 |
| Epothilone B | 4 mg/kg, i.v. every 7 days | 1 | −8% (transient) | 29 ± 16 | −1.2 ± 0.6 | −5 ± 3 | 3/6 |
| Epothilone B | 2 mg/kg, i.v. every 7 days | 40 | none | 227 ± 76 | −3.5 ± 1.6 | −14 ± 6 | 5/6 |
| Epothilone B | 1 mg/kg, i.v. every 7 days | 86 | none | 393 ± 135 | 0.3 ± 1.2 | 2 ± 5 | 4/6 |

Tumor fragments of approximately 25 mg are implanted into the left flank of each female nude mouse (n = 6 per group); a subcutaneous estrogen pellet is placed in the opposite flank.
Treatments are started on day 19 after tumor transplantation.
epothilone B is administered at 1, 2 or 4 mg/kg, i.v., either once per week (days 19, 26 and 33) or every second week (days 19 and 33).
Data presented are from animals surviving to day 47, the last day of controls.
Antitumor activity is expressed as T/C % (mean increase of tumor volumes of treated animals divided by the mean increase of tumor volumes of control animals multiplied by 100).
Tumor regression (%) represents the final mean tumor volume compared to the mean tumor volume at the start of treatment.
Changes (Δ) in tumor volume represent the tumor volume on the last treatment day minus the tumor volume on the first treatment day.

Example 10

Antitumor Effect of Epothilone B in Comparison With 5-Fluorouracil Against subcuntaneously Transplanted Colo 205 Colon Tumors Table 11 shows the effect of epothilone B against subcutaneously transplanted Colo 205 tumors, as well as the effect of 5-fluorouracil. In contrast to the treatment of the HCT-15 cell line tumors, where standard treatment with 5-fluorouracil or treatment with TAXOL® is not effective, here the treatment with 5-fluorouracil is still effective, though much less so than with epothilone B.

Together with the data from example 4 where the HCT-15 cells do not respond to (are refractory to) both TAXOL® and the standard colon cancer treatment with 5-fluorouracil, this shows that epothilone B is indeed appropriate to treat tumors that are refractory to known standard treatments. On the other hand, it is also more effective where standard treatments work. A preferred treatment schedule can be deduced which is 4 mg/kg every 2 weeks (tumor regression, no dead animals). This treatment is even better than that with 5-fluorouracil where no regression is found, but only 4 out of 7 animals survive.

Example 11

A Phase 1, Dose-Finding Study of Single Agent Epothilone B Administered Once Every Week to Adult Patients With Advanced Solid Tumors Number of centers 2

Objectives

Primary: To characterize the safety profile, including both acute and cumulative toxicities, and determine the maximum tolerated dose of single agent epothilone B administered by intravenous infusion once every week to adult patients with advanced solid tumors who have failed standard systemic therapy or for whom standard systemic therapy does not exist.

Secondary: 1. To characterize the pharmacokinetics of single agent epothilone B administered by intravenous infusion once every week to this population of patients; data obtained are used in concert with pharmacodynamic data (e.g. hematologic parameters), to make pharmacokinetic/pharmacodynamic (PK/PD) correlations that help predict safety and efficacy.

TABLE 11

Antitumor effect of epothilone B in comparison with 5-fluorouracil against subcutaneously transplanted human COLO 205 colon tumors in female BALB/c nude mice (day 32, four days post last treatment).

| Compound | Dose, Route, Schedule | Tumor Response | | | Host Response | | |
|---|---|---|---|---|---|---|---|
| | | T/C | Regression | Δ Tumor Volume (mm³) | Δ Body Weight (g) | % Body Weight Change | Survival (No. alive/total) |
| Vehicle controls | 25 ml/kg, i.v. every 7 days | 100% | none | 380 ± 96 | 2.7 ± 0.3 | 11 ± 2 | 7/7 |
| Epothilone B | 4 mg/kg, i.v. every 14 days | Regressions | −69% | −62 ± 7 | −1.1 ± 1.0 | −4 ± 4 | 7/7 |
| Epothilone B | 4 mg/kg, i.v. every 7 days | Regressions | −87% | −83 ± 7 | −4.0 ± 0.2 | −18 ± 1 | 5/7 |
| Epothilone B | 4 mg/kg, i.v. once | Regressions | −66% | −58 ± 11 | 2.0 ± 0.1 | 9 ± 1 | 5/7 |
| 5-Fluorouracil | 75 mg/kg, i.v. every 7 days | 18 | none | 62 ± 12 | 2.2 ± 0.4 | 9 ± 2 | 4/7 |

Tumor fragments of approximately 25 mg are implanted into the left flank of each female nude mouse (n = 7 per group); a subcutaneous estrogen pellet is placed on the opposite flank.

Treatments are started on day 14 after tumor transplantation.

epothilone B is administered at 4 mg/kg, i.v., either once or once per week (days 14, 21, 28) or every second week (days 14 and 28).

5-fluorouracil is administered i.v. at 75 mg/kg on days 14, 21, 28.

Data presented are from animals surviving to day 32, four days after the last treatments.

Antitumor activity is expressed as T/C % (mean increase of tumor volumes of treated animals divided by the mean increase of tumor volumes of control animals multiplied by 100).

Tumor regression (%) represents the final mean tumor volume compared to the mean tumor volume at the start of treatment.

Changes (Δ) in tumor volumes represent the tumor volume on the last treatment day minus the tumor volume on the first treatment day.

2. To obtain preliminary evidence of antitumor activity of single agent epothilone B administered by intravenous infusion once every week to this population of patients.
3. To correlate intratumor drug levels between adult patients with advanced solid tumors receiving single agent epothilone B by intravenous infusion once every week, to those associated with efficacy in pre-clinical models.
4. To gather pharmacogenetic information on tumors on tumor biopsy samples where available and accessible pre- and post-therapy in order to identify genes that correlate with efficacy and response; this is performed either by genetic analysis of individual gene expression (e.g. p53, Map4, and mdr1 expression status) or by gene chip technology.

Design This is an open-label, dose-escalation study to assess the safety, pharmacokinetics, and pharmacodynamics of epothilone B administered by intravenous infusion once every week to adult patients with advanced solid tumors who have failed standard systemic therapy or for whom standard systemic therapy does not exist.

The treatment period consists of up to 24 weekly doses. Patients experiencing unacceptable toxicity or disease progression are discontinued prematurely. Patients achieving a complete or partial response, or patients with stable disease at the end of 24 doses continue further treatment according to an extension protocol at the discretion of the investigator and after approval by the sponsor. Eligible patients receive additional cycles until disease progression or unacceptable toxicity.

The standard Phase 1 protocol design of enrolling 3-6 patients per cohort to establish the MTD is employed. Dose escalation proceed according to a modified Fibonacci scheme and is based on toxicities from the first 4 weekly doses for each cohort of patients. The starting dose is 0.1 mg/m$^2$, with subsequent doses as follows: 0.2, 0.3, 0.5, 0.7, and 0.9 mg/m$^2$.

The provisional MTD are defined as the dose level immediately below that at which dose limiting toxicity (DLT) is observed in at least two out of 3-6 patients. The cohort defined as the provisional MTD then enrolls additional patients to a total of 12 to confirm the MTD through further evaluation of the safety, pharmacokinetic, and pharmacodynamic profiles of epothilone B.

All toxicities are defined according to the revised US National Cancer Institute Common Toxicity Criteria. DLTs are defined in the protocol; in general, however, the nature of a DLT is such that it is considered unacceptable even in the setting of an incurable solid tumor.

Patients

Inclusion Criteria

The following criteria are to be met for inclusion into the study:
1. Male or female patients ≧18 years of age.
2. Histologically documented advanced solid tumor, who have failed standard systemic therapy and up to 1 additional systemic therapy, or for whom standard systemic therapy does not exist.
3. At least one measurable, evaluable, or non-evaluable site of disease as defined by Southwestern Oncology Group (SWOG) Solid Tumor Response Criteria including tumor marker value that is above the institutional upper limit of normal.
4. Women of childbearing potential must have a negative serum β-HCG pregnancy test prior to the initiation of study drug. Male and female patients of reproductive potential must agree to employ an effective method of birth control throughout the study and for up to 3 months following discontinuation of study drug.
5. World Health Organization (WHO) Performance Status Score of ≦2.
6. Life expectancy of at least 3 months.
7. Written informed consent obtained prior to any screening procedures.

Exclusion Criteria

Exclusion from the study is required if any of the following apply:
1. Female patients who are pregnant or breast-feeding. Postmenopausal women must be amenorrheic for at least 12 months to be considered of non-childbearing potential.
2. Patient has a severe and/or uncontrolled medical disease (i.e., uncontrolled diabetes, congestive heart failure, myocardial infarction within 6 months of study, chronic renal disease, or active uncontrolled infection);
3. Patient has a known brain metastasis.
4. Patient has an acute or known chronic liver disease (i.e., chronic active hepatitis, cirrhosis).
5. Patient has a known diagnosis of human immunodeficiency virus (HIV) infection.
6. Patient has received any investigational agent within 30 days prior to study entry.
7. Patient received chemotherapy within 4 weeks (6 weeks for nitrosoureas or mitomycin C) prior to study entry.
8. Patient received prior radiation therapy within 4 weeks prior to study entry.
9. Patient previously received radiotherapy to ≧25% of the bone marrow.
10. Patient had a major surgery within 2 weeks prior to study entry.
11. Patient has a history of non-compliance to medical regimens.
12. Patient has impairment of hepatic, renal or hematologic function as defined by the following laboratory parameters:
   Platelet count <100×10$^9$/L
   Absolute neutrophil count (ANC) <1.5×10$^9$/L
   Serum ALT (SGPT) >2.5×institutional upper limit of normal (IULN)
   Serum total bilirubin >1.5×IULN
   Serum creatinine >1.5×IULN
13. Patient is <5 years free of another primary malignancy or, in the case of non-melanomatous skin cancer and cervical carcinoma in situ, has active disease.

Sample size This study requires about 40 patients.

Treatments Epothilone B is supplied in individual 2 ml glass vials formulated as 1 mg/1 ml of the clear, colorless intravenous concentrate. The substance is formulated in polyethylene glycol 300 (PEG 300) and diluted with 50 to 100 ml 0.9% Sodium Chloride Injection, USP, to achieve the desired final concentration of the drug for infusion. It is administered as a single 30-minute intravenous infusion every 7 days.

The starting dose level is 0.1 mg/m$^2$. This dose is calculated as one-third of the toxic dose low (TDL) in the most sensitive species studied which, for epothilone B, is the dog. As described above, dose escalation proceeds according to a modified Fibonacci scheme. The study defines treatment delays, dose reductions, or withdrawal from treatment for individuals experiencing hematologic or other toxicities known to result from epothilone B. Treatment continues to a maximum of 24 weekly doses unless the patient experiences disease progression or unacceptable toxicity. At the end of 24 doses, patients who have achieved a complete or partial response and patients who have had stable disease may continue further treatment according to an extension protocol at the discretion of the investigator and after approval by the sponsor.

Safety

Variables The safety of epothilone B is assessed by physical examination and evaluation of vital signs, clinical laboratory results, adverse events, and use of concomitant medications. Adverse events are both elicited and volunteered and are graded using the revised US National Cancer Institute Expanded Common Toxicity Criteria.

Efficacy

Variables Although this phase 1 study is not designed to detect efficacy, activity is demonstrated as a function of the rate of objective tumor response and length of progression-free and overall survival. Baseline tumor evaluations include optimal assessment of all measurable, evaluable, and non-evaluable disease. Evaluations include physical examination and chest roentgenogram and, as appropriate, computerized tomogram of the thorax, abdomen and pelvis; sonogram of the abdomen and pelvis; bone scintigram, with bone roentgenogram of all known osseous lesions; and determination of tumor marker values. Follow-up studies are obtained every 6 weeks and after cessation of treatment.

Objective status is clinically evaluated using the Novartis guidelines, which are based on the SWOG response criteria. All complete-and partial responses must be confirmed by a second assessment at least four weeks later. Best tumor response are calculated for each patient using the SWOG response criteria.

Pharmacokinetics The following pharmacokinetic parameters are calculated and analyzed for cycles 1 and 2: $t_{max}$, $C_{max}$, $\lambda_Z$, $t_{1/2}$, AUC, and $R_A$. $R_A$=the ratio of $AUC\tau_{cycle2}/AUC\tau_{cycle1}$ is evaluated as an index of accumulation. Preliminary assessment of dose proportionality is based on AUC from the last dose among different dose groups. PK/PD correlations with observed toxicities (e.g., hematopoietic) are performed as a predictor of safety.

Pharmacodynamics Tumor biopsy samples are obtained where feasible and accessible, pre-therapy and after the first cycle of therapy. These biopsy samples are prepared for analysis of their gene expression using gene chip technology, then separately analyzed for p53 status, MAP4 RNA expression, and mdr1 RNA expression.

Statistical methods Patients with treatment-emergent clinical adverse events (especially those with dose-limiting toxicity) or with laboratory, vital sign, or physical examination abnormalities (newly occurring or worsening from baseline) are identified and the values are flagged. The rate of abnormalities is tabulated by cohort. Objective response rates (including both complete and partial responses) are presented by cohort. Descriptive statistics are used to summarize the basic pharmacokinetic parameters by cohort.

Example 12

A Phase 1, Dose-Finding Study of Single Agent EPO906 (Epothilone B Administered Once Every Three Weeks to Adult Patients with Advanced Solid Tumors No. of Centers: 2
Locations Glasgow, UK, & Newcastle, UK
Objectives
 Primary: To characterize the safety profile, including both acute and cumulative toxicities, and determine the maximum tolerated dose of single agent epothilone B administered by intravenous infusion once every three weeks to adult patients with advanced solid tumors who have failed standard systemic therapy or for whom standard systemic therapy does not exist
 Secondary: 1. To characterize the pharmacokinetics of single agent epothilone B administered by intravenous infusion once every three weeks to this population of patients; data obtained are used in concert with pharmacodynamic data to make pharmacokinetic/pharmacodynamic (PK/PD) correlations that help predict safety and efficacy
 2. To obtain preliminary evidence of antitumor activity of single agent epothilone B administered by intravenous infusion once every three weeks to this population of patients
 3. To correlate intratumor drug levels between adult patients with advanced solid tumors receiving single agent epothilone B by intravenous infusion once every three weeks to those associated with efficacy in preclinical models
 4. To gather information on tumors from tumor biopsy samples where available and accessible pre- and post-therapy in order to identify biological factors that correlate with efficacy and response
Design This is an open-label, dose-escalation study to assess the safety, pharmacokinetics, and pharmacodynamics of epothilone B administered by intravenous infusion once every three weeks to adult patients with advanced solid tumors who have failed standard systemic therapy or for whom standard systemic therapy does not exist.
 The treatment period consists of up to six 21-day cycles. Patients experiencing unacceptable toxicity or disease progression are discontinued prematurely. Patients achieving a complete or partial response, or patients with stable disease at the end of six cycles continue further treatment according to an extension protocol at the discretion of the investigator and after approval by the sponsor. Eligible patients receive additional cycles until disease progression or unacceptable toxicity are observed.
 In the absence of dose-limiting toxicity (DLT), dose escalation proceeds as follows:
 1. First dose escalation: 100% dose increase (unless grade 2 toxicity is identified in first cohort, in which case dose escalation is 25%-67%)
 2. Dose escalations following 100% dose increase from first to second cohort: 67% dose increases until grade 2 toxicity is identified
 3. Final dose escalations following identification of grade 2 toxicity: 25%-67% dose increases, based on consensus reached among the investigators and the sponsor
Dose escalation is based on toxicities from the first cycle for each cohort of patients. The provisional maximum tolerated dose (MTD) is defined as the dose level immediately below that at which DLT is observed in at least two out of 3-6 patients. The cohort defined as the provisional MTD then enrolls additional patients to a total of 12 to confirm the MTD through further evaluation of the safety, pharmacokinetic, and pharmacodynamic profiles of epothilone B.

Intrapatient dose escalation will not be permitted.

All toxicities are defined according to the revised US National Cancer Institute Common Toxicity Criteria. DLTs are defined in the protocol; in general, however, the nature of a DLT is such that it is considered unacceptable even in the setting of an incurable solid tumor.

Patients

Inclusion Criteria

The following criteria must be met for inclusion into the study:
1. Male or female patients >18 years of age.
2. Histologically documented advanced solid tumor, who have failed standard systemic therapy and up to 1 additional systemic therapy, or for whom standard systemic therapy does not exist.
3. At least one measurable, evaluable, or non-evaluable site of disease as defined by Southwestern Oncology Group (SWOG) Solid Tumor Response Criteria including tumor marker value that is above the institutional upper limit of normal.
4. Women of childbearing potential must have a negative serum β-HCG pregnancy test prior to the initiation of study drug. Male and female patients of reproductive potential must agree to employ an effective method of birth control throughout the study and for up to 3 months following discontinuation of study drug.
5. World Health Organization (WHO) Performance Status Score of $\leq 2$.
6. Life expectancy of at least 3 months.
7. Written informed consent is obtained prior to any screening procedures.

Exclusion Criteria

Exclusion from the study is required if any of the following apply:
1. Female patients who are pregnant or breast-feeding. Postmenopausal women must be amenorrheic for at least 12 months to be considered of non-childbearing potential.
2. Patient has a severe and/or uncontrolled medical disease (i.e., uncontrolled diabetes, congestive heart failure, myocardial infarction within 6 months of study, chronic renal disease, or active uncontrolled infection).
3. Patient has a known brain metastasis.
4. Patient has an acute or known chronic liver disease (i.e., chronic active hepatitis, cirrhosis).
5. Patient has a known diagnosis of human immunodeficiency virus (HIV) infection.
6. Patient has received any investigational agent within 30 days prior to study entry.
7. Patient received chemotherapy within 4 weeks (6 weeks for nitrosoureas or mitomycin C) prior to study entry.
8. Patient received prior radiation therapy within 4 weeks prior to study entry.
9. Patient previously received radiotherapy to $\geq 25\%$ of the bone marrow.
10. Patient had a major surgery within 2 weeks prior to study entry.
11. Patient has a history of non-compliance to medical regimens.
12. Patient has impairment of hepatic, renal or hematologic function as defined by the following laboratory parameters:
    Platelet count <100×10$^9$/L
    Absolute neutrophil count (ANC) <1.5×10$^9$/L
    Serum ALT (SGPT) or AST (SGOT) >2.5×institutional upper limit of
    normal (IULN) (>5×IULN for patients with hepatic metastases)
    Serum total bilirubin >1.5×IULN
    Serum creatinine >1.5×IULN
13. Patient is <5 years free of another primary malignancy; however, non-melanomatous skin cancer and cervical carcinoma in situ are excluded only if the patient has active disease.

Sample size This study requires about 40 patients.

Treatments epothilone B is supplied in individual 2 ml glass vials formulated as 1 mg/1 ml of the clear, colorless intravenous concentrate. The substance is formulated in polyethylene glycol 300 (PEG 300) and diluted with 50 or 100 ml 0.9% Sodium Chloride Injection, USP, to achieve the desired final concentration of the drug for infusion. It is administered as a single 30-minute intravenous infusion every 21 days for six cycles.

The starting dose level is 0.3 mg/m$^2$. This dose is calculated as one-third of the toxic dose low (TDL) in the most sensitive species studied which, for epothilone B, is the dog. Since there are no mortalities at the lower of the 2 doses administered to dogs in the GLP toxicology study—0.1 mg/kg, repeated once 3 weeks later—the TDL is estimated to be in the range of 0.65 mg/kg. Using a factor of 20 to convert mg/kg in the dog to mg/m$^2$ in humans, this starting dose is calculated as:

$$\frac{1}{3} \times 0.05 \text{ mg/kg} \times 20 \text{ kg/m}^2 = 0.3 \text{ mg/m}^2$$

Dose escalation proceeds according to the scheme outlined above.

The study defines treatment delays, dose reductions, or withdrawal from treatment for individuals experiencing hematologic or other toxicities known to result from epothilone B. Treatment continues to a maximum of 6 cycles unless the patient experiences disease progression or unacceptable toxicity.

At the end of 6 cycles, patients who have achieved a complete or partial response and patients who have had stable disease may continue further treatment according to an extension protocol at the discretion of the investigator and after approval by the sponsor.

Safety variables The safety of epothilone B is assessed by physical examination and evaluation of vital signs, clinical laboratory results, adverse events, and use of concomitant medications. Adverse events are both elicited and volunteered and are graded using the revised US National Cancer Institute Common Toxicity Criteria.

Efficacy variables Although this phase 1 study is not designed to detect efficacy, activity is demonstrated as a function of the rate of objective tumor response and length of progression-free and overall survival. Baseline tumor evaluations include optimal assessment of all measurable, evaluable, and non-evaluable disease. Evaluations include physical examination and chest roentgenogram and, as appropriate, computerized tomogram of the thorax, abdomen and pelvis; sonogram of the abdomen and pelvis; bone scintigram, with bone roentgenogram of all known osseous lesions;

and determination of tumor marker values. Follow-up studies are obtained every two cycles and after cessation of treatment.

Objective status is clinically evaluated using the Novartis guidelines, which are based on the SWOG response criteria. All complete and partial responses must be confirmed by a second assessment at least four weeks later. Best tumor response are calculated for each patient using the SWOG response criteria.

Pharmacokinetics The following pharmacokinetic parameters are calculated and analyzed for cycles 1 and 2: $t_{max}$, $C_{max}$, $\lambda_Z$, $t_{1/2}$, AUC, and $R_A$. $R_A$=the ratio of $AUC\tau_{cycle2}/AUC\tau_{cycle1}$ is evaluated as an index of accumulation. Preliminary assessment of dose proportionality is based on AUC from the last dose among different dose groups. PK/PD correlations with observed toxicities (e.g., hematopoietic) are performed as a predictor of safety.

Pharmacodynamics Tumor biopsy samples are obtained where feasible and accessible prethereapy and after the first cycle of therapy in order to identify biological factors that correlate with efficacy and response.

Statistical methods Patients with treatment-emergent clinical adverse events (especially those with dose-limiting toxicity) or with laboratory, vital sign, or physical examination abnormalities (newly occurring or worsening from baseline) are identified and the values are flagged. The rate of abnormalities is tabulated by cohort. Objective response rates (including both complete and partial responses) are presented by cohort. Descriptive statistics are used to summarize the basic pharmacokinetic parameters by cohort.

Discussion: Taken together, the examples provide evidence that treatment with epothilone B is effective
a) also against a tumor where standard treatment fails, e.g. in colon tumor where 5-fluorouracil treatment fails, or where TAXOL® treatment fails;
b) also against a tumor where TAXOL® treatment fails, e.g. lung, especially non-small cell lung cancer, and/or epidermoid, especially cervical, tumors;
c) also against orthotopic tumors and the formation of metastases, e.g. in prostate tumors;
d) also against breast cancer where in in vitro assays (example 3) epothilone B shows higher activity than TAXOL®.

The preferred dosage regimens center around an area of weekly treatment with about ⅓ to ⅔ of the MTD up to treatment once with a dose up to the MTD, with a kind of best treatment area lying at the weekly up to three-weekly administration.

What we claim is:

1. A method of treating a human patient suffering from a tumor disease selected from ovarian cancer, the method comprising administering to the patient two or more doses of epothilone B in an amount that is sufficient to treat the tumor, wherein the second and any subsequent dose is administered more than a week after the immediately preceding dose, and wherein no single dose exceeds 18 mg/m².

2. The method of 1, wherein the second and any subsequent dose is administered more than two weeks after the immediately preceding dose.

3. The method of claim 1, wherein the second and any subsequent dose is administered between three to six weeks after the immediately preceding dose.

4. The method of claim 1, wherein the second and any subsequent dose is administered about two weeks after the immediately preceding dose.

5. The method of claim 1, wherein the second and any subsequent dose is administered three weeks after the immediately preceding dose.

6. The method of claim 1, wherein the second and any subsequent dose is administered between 18 and 24 days after the immediately preceding dose.

7. The method of claim 1, wherein the number of doses is at least three.

8. The method of claim 1, wherein the number of doses is at least four.

9. The method of claim 1, wherein the number of doses is at least six.

10. The method of claim 1, wherein the number of doses is at least eight.

11. The method of claim 6, wherein the tumor is a multi-drug resistant cancer.

12. The method of claim 6, wherein the tumor is refractory to treatment with a member of the taxane class of anticancer agents.

13. The method of claim 6, wherein the tumor is refractory to treatment with paclitaxel.

14. The method of claim 6, wherein epothilone B is administered in a composition comprising epothilone B, polyethylene glycol (PEG), and sodium chloride.

15. The method of claim 1, wherein epothilone B is administered intravenously.

16. The method of claim 15, wherein epothilone B is administered by infusion.

17. The method of claim 16, wherein each dose of epothilone B is administered by intravenous infusion over a period of 2 to 120 minutes.

18. The method of claim 16, wherein each dose of epothilone B is administered by intravenous infusion over a period of 5 to 30 minutes.

19. The method of claim 16, wherein the second and any subsequent dose is administered between 18 and 24 days after the immediately preceding dose.

20. The method of claim 6, wherein epothilone B is administered every third week in a dose of between about 0.3 and about 18 mg/m².

21. The method of claim 6, wherein epothilone B is administered every third week in a dose of between about 0.3 and about 15 mg/m².

22. The method of claim 6, wherein epothilone B is administered every third week in a dose of between about 0.3 and about 12 mg/m2.

23. The method of claim 6, wherein epothilone B is administered every third week in a dose of between about 0.3 and about 7.5 mg/m².

24. The method of claim 1, wherein epothilone B is administered every third week in a dose of between about 0.3 and about 5 mg/m².

25. The method of claim 1, wherein epothilone B is administered every third week in a dose of between about 1.0 and about 3.0 mg/m².

26. The method of claim 1, wherein epothilone B is administered every 18 to 24 days in a dose of between about 0.3 and about 18 mg/m².

27. The method of claim 1, wherein epothilone B is administered every 18 to 24 days in a dose of between about 0.3 and about 15 mg/m².

28. The method of claim 1, wherein epothilone B is administered every 18 to 24 days in a dose of between about 0.3 and about 12 mg/m².

29. The method of claim 1, wherein epothilone B is administered every 18 to 24 days in a dose of between about 0.3 and about 7.5 mg/m².

30. The method of claim 1, wherein epothilone B is administered every 18 to 24 days in a dose of between about 0.3 and about 5 mg/m².

31. The method of claim 1, wherein epothilone B is administered every 18 to 24 days in a dose of between about 1.0 and about 3.0 mg/m$^2$.

32. The method of claim 1, wherein each dose of epothilone B is administered by intravenous infusion over a period of 2 to 180 minutes.

33. The method of claim 1, wherein each dose of epothilone B is administered by intravenous infusion over a period of 10 to about 30 minutes.

34. The method of claim 1, wherein each dose of epothilone B is administered by intravenous infusion over a period of about 30 minutes.

35. The method of claim 1, wherein the tumor is refractory to treatment with 5-fluorouracil.

36. The method of claim 1, wherein the amount of epothilone B administered in each dose is calculated according to the formula:

$$\text{single dose (mg/m}^2\text{)} = (0.1 \text{ to } y) \times N$$

where N is the number of weeks that elapse between administration of two sequential doses and y is 6.

* * * * *